(12) United States Patent
Causey et al.

(10) Patent No.: US 8,057,436 B2
(45) Date of Patent: Nov. 15, 2011

(54) DISPENSING FLUID FROM AN INFUSION PUMP SYSTEM

(75) Inventors: James Causey, Simi Valley, CA (US); Todd Kirschen, Fullerton, CA (US); Mitchell Wenger, Chicago, IL (US); Steven Friedman, San Francisco, CA (US); Joshua Colton, Palo Alto, CA (US); Keld Sloth Christensen, Hjerm (DK)

(73) Assignee: Asante Solutions, Inc., Sunnyvale, CA (US)

( * ) Notice: Subject to any disclaimer, the term of this patent is extended or adjusted under 35 U.S.C. 154(b) by 1282 days.

(21) Appl. No.: 11/677,706

(22) Filed: Feb. 22, 2007

(65) Prior Publication Data

US 2007/0179444 A1    Aug. 2, 2007

(51) Int. Cl.
*A61M 1/00* (2006.01)
(52) U.S. Cl. .......................... 604/151; 604/131
(58) Field of Classification Search .................. 604/131, 604/122, 67, 207, 181, 134, 218, 223
See application file for complete search history.

(56) References Cited

U.S. PATENT DOCUMENTS

| | | |
|---|---|---|
| 2,605,765 A | 8/1952 | Kollsman |
| 3,886,938 A | 6/1975 | Szabo et al. |
| 4,077,405 A | 3/1978 | Haerten et al. |
| 4,231,368 A | 11/1980 | Becker |
| 4,265,241 A | 5/1981 | Portner et al. |
| 4,300,554 A | 11/1981 | Hessberg et al. |
| 4,313,439 A | 2/1982 | Babb et al. |
| 4,398,908 A | 8/1983 | Siposs |
| 4,435,173 A | 3/1984 | Siposs et al. |
| 4,443,218 A | 4/1984 | DeCant, Jr. et al. |
| 4,493,704 A | 1/1985 | Beard et al. |
| 4,529,401 A | 7/1985 | Leslie et al. |
| 4,850,817 A | 7/1989 | Nason et al. |
| 5,045,064 A | 9/1991 | Idriss |
| 5,088,981 A | 2/1992 | Howson et al. |
| 5,190,522 A | 3/1993 | Wojcicki et al. |
| 5,250,027 A | 10/1993 | Lewis et al. |
| 5,261,882 A | 11/1993 | Sealfon et al. |
| 5,314,412 A | 5/1994 | Rex |
| 5,335,994 A | 8/1994 | Weynant Nee Girones |
| 5,338,157 A | 8/1994 | Blomquist |
| 5,342,180 A | 8/1994 | Daoud |
| 5,395,340 A | 3/1995 | Lee |
| 5,411,487 A | 5/1995 | Castagna |
| 5,545,143 A | 8/1996 | Fischell et al. |
| 5,551,850 A | 9/1996 | Williamson et al. |
| 5,569,186 A | 10/1996 | Lord et al. |

(Continued)

FOREIGN PATENT DOCUMENTS

CA    2543545    5/2005

(Continued)

OTHER PUBLICATIONS

International Preliminary Report on Patentability, PCT/US2007/062586, mailed Sep. 3, 2009, 11 pages.

(Continued)

*Primary Examiner* — Theodore Stigell
*Assistant Examiner* — Brandy C Scott
(74) *Attorney, Agent, or Firm* — Fish & Richardson P.C.

(57) ABSTRACT

Some embodiments of a medical infusion pump system include a drive system that advances a piston rod to dispense medicine to the patient in a safe and energy efficient manner.

34 Claims, 14 Drawing Sheets

U.S. PATENT DOCUMENTS

| | | |
|---|---|---|
| 5,626,566 A | 5/1997 | Petersen et al. |
| 5,637,095 A | 6/1997 | Nason et al. |
| 5,665,065 A | 9/1997 | Colman et al. |
| 5,741,216 A | 4/1998 | Hemmingsen et al. |
| 5,772,635 A | 6/1998 | Dastur et al. |
| 5,816,306 A | 10/1998 | Giacomel |
| 5,852,803 A | 12/1998 | Ashby, III et al. |
| 5,919,167 A | 7/1999 | Mulhauser et al. |
| 5,925,018 A | 7/1999 | Ungerstedt |
| 5,928,201 A | 7/1999 | Poulsen et al. |
| 5,947,934 A | 9/1999 | Hansen et al. |
| 5,951,530 A | 9/1999 | Steengaard et al. |
| 5,957,889 A | 9/1999 | Poulsen et al. |
| 5,984,894 A | 11/1999 | Poulsen et al. |
| 5,984,897 A | 11/1999 | Petersen et al. |
| 5,997,475 A | 12/1999 | Bortz |
| 6,003,736 A | 12/1999 | Ljunggren |
| 6,010,485 A | 1/2000 | Buch-Rasmussen et al. |
| 6,033,377 A | 3/2000 | Rasmussen et al. |
| 6,045,537 A | 4/2000 | Klitmose |
| 6,074,372 A | 6/2000 | Hansen |
| 6,110,149 A | 8/2000 | Klitgaard et al. |
| 6,156,014 A | 12/2000 | Petersen et al. |
| 6,171,276 B1 | 1/2001 | Lippe et al. |
| 6,231,540 B1 | 5/2001 | Smedegaard |
| 6,248,067 B1 | 6/2001 | Causey, III et al. |
| 6,248,090 B1 | 6/2001 | Jensen et al. |
| 6,248,093 B1 | 6/2001 | Moberg |
| 6,277,098 B1 | 8/2001 | Klitmose et al. |
| 6,302,855 B1 | 10/2001 | Lav et al. |
| 6,302,869 B1 | 10/2001 | Klitgaard |
| 6,375,638 B2 | 4/2002 | Nason et al. |
| 6,379,339 B1 | 4/2002 | Klitgaard et al. |
| 6,381,496 B1 | 4/2002 | Meadows et al. |
| 6,404,098 B1 | 6/2002 | Kayama et al. |
| 6,427,088 B1 | 7/2002 | Bowman, IV et al. |
| 6,461,331 B1 | 10/2002 | Van Antwerp |
| 6,474,219 B2 | 11/2002 | Klitmose et al. |
| 6,485,461 B1 | 11/2002 | Mason et al. |
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |
| 6,540,672 B1 | 4/2003 | Simonsen et al. |
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,605,067 B1 | 8/2003 | Larsen |
| 6,613,019 B2 | 9/2003 | Munk |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 | 12/2003 | Møller |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman, IV et al. |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larsen et al. |
| 7,014,625 B2 | 3/2006 | Bengtsson |
| 7,018,360 B2 | 3/2006 | Flaherty et al. |
| 7,025,743 B2 | 4/2006 | Mann |
| 7,029,455 B2 | 4/2006 | Flaherty |
| 7,054,836 B2 | 5/2006 | Christensen et al. |
| 7,104,972 B2 | 9/2006 | Møller et al. |
| 7,128,727 B2 | 10/2006 | Flaherty et al. |
| 7,133,329 B2 | 11/2006 | Skyggebjerg et al. |
| 7,232,423 B2 | 6/2007 | Mernoe |
| 2001/0056262 A1 | 12/2001 | Cabiri |
| 2002/0004651 A1 | 1/2002 | Ljndggreen et al. |
| 2002/0007154 A1 | 1/2002 | Hansen et al. |
| 2002/0040208 A1 | 4/2002 | Flaherty et al. |
| 2002/0091358 A1 | 7/2002 | Klitmose |
| 2002/0126036 A1 | 9/2002 | Flaherty et al. |
| 2003/0055380 A1 | 3/2003 | Flaherty |
| 2003/0065308 A1 | 4/2003 | Lebel et al. |
| 2003/0088238 A1 | 5/2003 | Poulsen |
| 2003/0199825 A1 | 10/2003 | Flaherty |
| 2003/0216683 A1 | 11/2003 | Shekalim |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0116866 A1 | 6/2004 | Gorman et al. |

| | | | | | | |
|---|---|---|---|---|---|---|
| 2004/0127844 A1 | 7/2004 | Flaherty | | FR | 2 585 252 | 1/1987 |
| 2004/0153032 A1 | 8/2004 | Garribotto et al. | | GB | 747 701 | 4/1956 |
| 2004/0171983 A1 | 9/2004 | Sparks et al. | | GB | 2 218 831 | 11/1989 |
| 2004/0176727 A1 | 9/2004 | Shekalim | | WO | WO 90/15928 | 12/1990 |
| 2004/0204673 A1 | 10/2004 | Flaherty | | WO | WO 97/21457 | 6/1997 |
| 2004/0220551 A1 | 11/2004 | Flaherty et al. | | WO | WO 98/11927 | 3/1998 |
| 2004/0235446 A1 | 11/2004 | Flaherty et al. | | WO | WO 98/57683 | 12/1998 |
| 2004/0260233 A1 | 12/2004 | Garibotto et al. | | WO | WO 99/21596 | 5/1999 |
| 2005/0021005 A1 | 1/2005 | Flaherty et al. | | WO | WO 99/39118 | 8/1999 |
| 2005/0022274 A1 | 1/2005 | Campbell et al. | | WO | WO 99/48546 | 9/1999 |
| 2005/0065760 A1 | 3/2005 | Murtfeldt et al. | | WO | WO 01/72360 | 10/2001 |
| 2005/0090808 A1 | 4/2005 | Malave et al. | | WO | WO 01/91822 | 12/2001 |
| 2005/0095063 A1 | 5/2005 | Fathallah | | WO | WO 01/91833 | 12/2001 |
| 2005/0160858 A1 | 7/2005 | Mernoe | | WO | WO 02/40083 | 5/2002 |
| 2005/0171512 A1 | 8/2005 | Flaherty | | WO | WO 02/057627 | 7/2002 |
| 2005/0182366 A1 | 8/2005 | Vogt et al. | | WO | WO 02/100469 | 12/2002 |
| 2005/0192561 A1* | 9/2005 | Mernoe ............. 604/890.1 | | WO | WO 03/103763 | 12/2003 |
| 2005/0203461 A1 | 9/2005 | Flaherty et al. | | WO | WO 2004/056412 | 7/2004 |
| 2005/0215982 A1 | 9/2005 | Malave et al. | | WO | WO 2004/110526 | 12/2004 |
| 2005/0222645 A1 | 10/2005 | Malave et al. | | WO | WO 2005/002652 | 1/2005 |
| 2005/0238507 A1 | 10/2005 | DiIanni et al. | | WO | WO 2005/039673 | 5/2005 |
| 2005/0245878 A1 | 11/2005 | Mernoe et al. | | WO | WO 2005/072794 | 8/2005 |
| 2005/0251097 A1 | 11/2005 | Mernoe | | WO | WO 2005/072795 | 8/2005 |
| 2005/0267402 A1 | 12/2005 | Stewart et al. | | WO | WO 2006/105792 | 10/2006 |
| 2005/0273059 A1 | 12/2005 | Mernoe et al. | | WO | WO 2006/105793 | 10/2006 |
| 2006/0041229 A1 | 2/2006 | Garibotto et al. | | WO | WO 2006/105794 | 10/2006 |
| 2006/0069382 A1 | 3/2006 | Pedersen | | | | |
| 2006/0074381 A1 | 4/2006 | Malave et al. | | | | |
| 2006/0095014 A1 | 5/2006 | Ethelfeld | | | | |
| 2006/0135913 A1 | 6/2006 | Ethelfeld | | | | |
| 2006/0142698 A1 | 6/2006 | Ethelfeld | | | | |
| 2006/0178633 A1 | 8/2006 | Garibotto et al. | | | | |
| 2006/0184119 A1 | 8/2006 | Remde et al. | | | | |
| 2006/0200073 A1 | 9/2006 | Radmer et al. | | | | |
| 2006/0206054 A1 | 9/2006 | Shekalim | | | | |
| 2006/0247581 A1 | 11/2006 | Pedersen et al. | | | | |
| 2007/0073228 A1 | 3/2007 | Mernoe et al. | | | | |
| 2007/0073236 A1 | 3/2007 | Mernoe et al. | | | | |
| 2007/0124002 A1 | 5/2007 | Estes et al. | | | | |
| 2007/0156092 A1 | 7/2007 | Estes et al. | | | | |
| 2007/0167905 A1 | 7/2007 | Estes et al. | | | | |
| 2007/0167912 A1 | 7/2007 | Causey et al. | | | | |
| 2008/0208627 A1 | 8/2008 | Skyggebjerg | | | | |

FOREIGN PATENT DOCUMENTS

| | | |
|---|---|---|
| DE | 196 27 619 A | 1/1998 |
| DE | 102 36 669 A | 2/2004 |
| EP | 0 496 141 | 7/1992 |
| EP | 0 612 004 | 8/1994 |
| EP | 0 580 723 | 10/1995 |
| EP | 1 045 146 | 10/2000 |
| EP | 1 136 698 | 9/2001 |
| EP | 1 177 802 | 2/2002 |
| EP | 0 721 358 | 5/2002 |
| EP | 1 495 775 | 1/2005 |
| EP | 1 527 792 | 5/2005 |
| EP | 1 754 498 | 2/2007 |

OTHER PUBLICATIONS

Collins and Lee, "Microfluidic flow transducer based on the measurement of electrical admittance," *Lab Chip*, 2004, 4:7-10.

Debiotech News Release, "Debiotech reveals its new miniaturized Disposable Insulin Nanopump™ for Diabetes therapy," available at http://www.debiotech.com/news/nw_159.html Apr. 24, 2006, 3 pages.

Patent Abstracts of Japan, vol. 1999, No. 04, and JP 11 010036, Apr. 30, 1999 and Jan. 19, 1999, Toray Ind. Inc.

Medtronic News Release, "Medtronic Receives FDA Approval for World's First Insulin Pump with Real-time Continuous Glucose Monitoring," Apr. 13, 2006, 3 pages.

International Search Report and Written Opinion PCT/US2007/062586, mailed Apr. 16, 2008, 20 pages.

Accu-Chek Spirit, "Pump Therapy Made for You," Roche, 2006, 6 pages.

Xilas Temp Touch, "The latest in high-tech and convenient devices," DOCNews, vol. 2, No. 7, Jul. 1, 2005, http://docnews.diabetesjournals.org/cgi/content/full/2/7/13, 3 pages.

The Medtronic Diabetes Connection, 2006, 6 pages.

OmniPod Insulin Management System-Investor Relations—Press Release, Feb. 1, 2005, http://investors.insulet.com/phoenix.zhtml?c=209336&p=irol-newsArticle&ID=988708&highlight= 1 page.

OmniPod Quick Start Guide, 2007, 2 pages.

U.S. Appl. No. 11/362,616.

\* cited by examiner

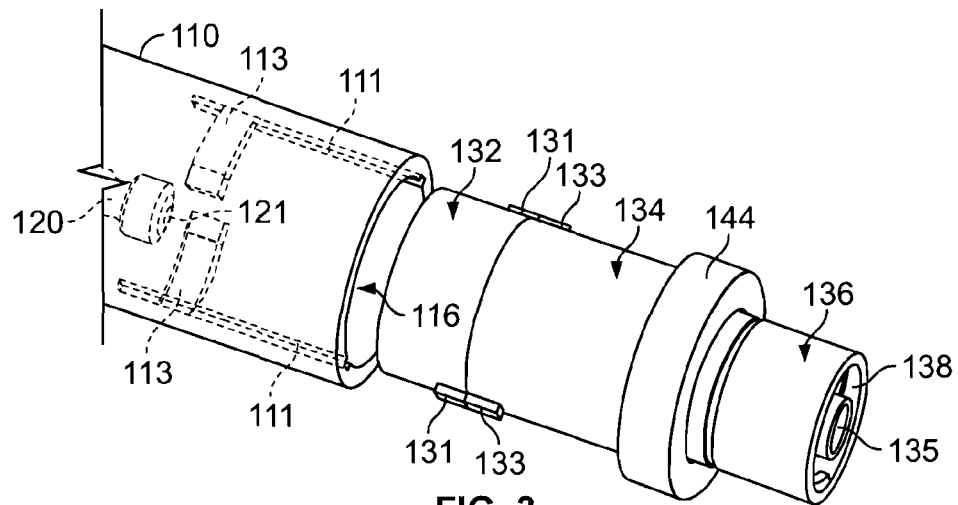
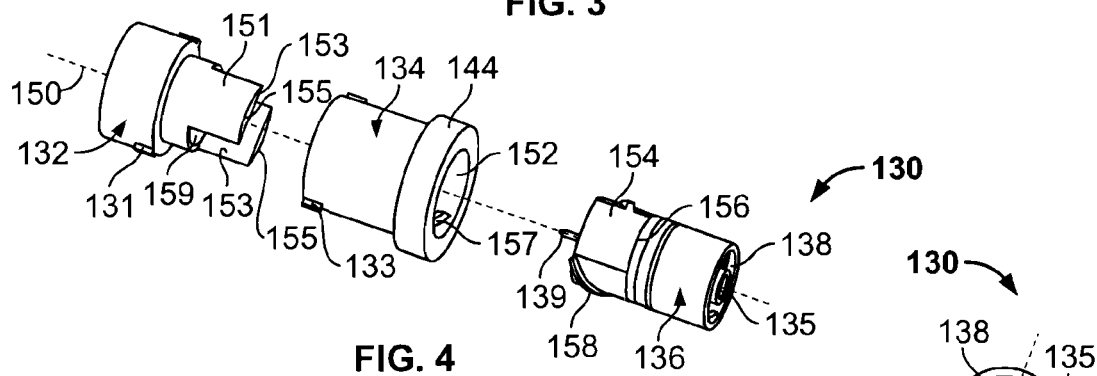
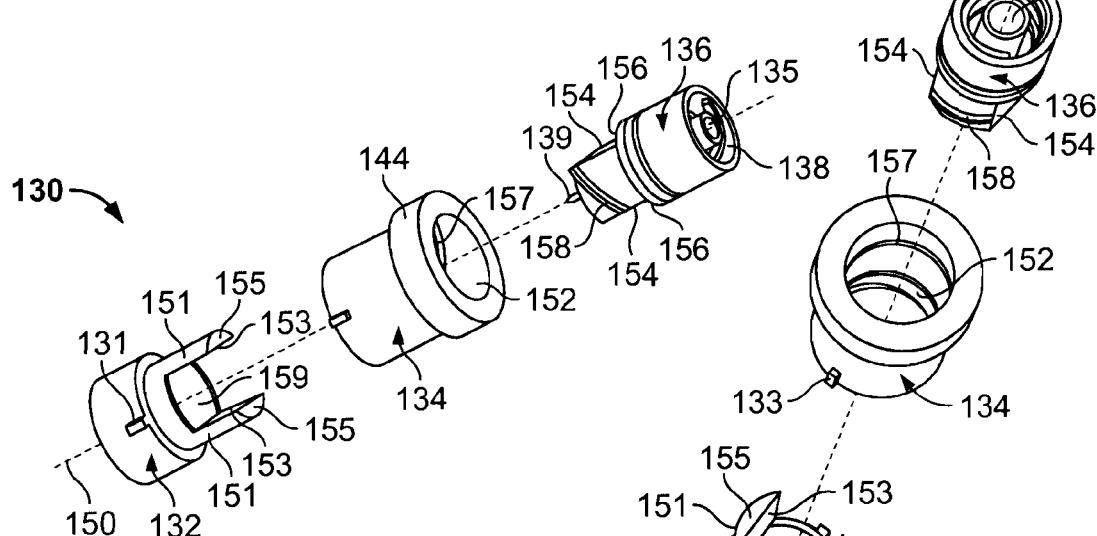
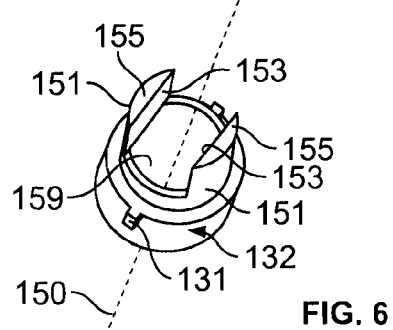

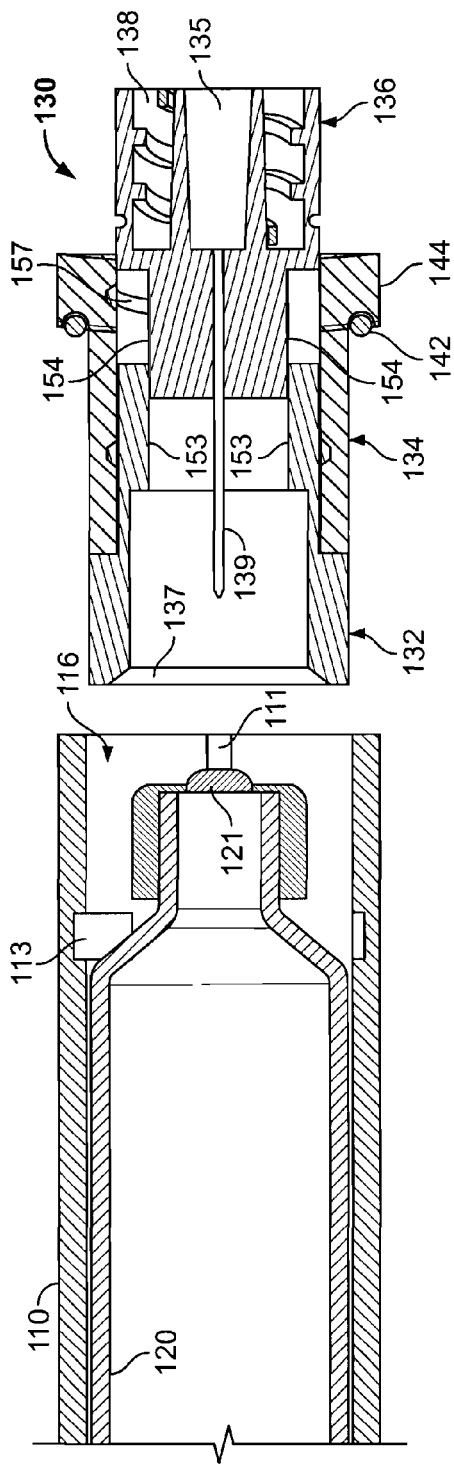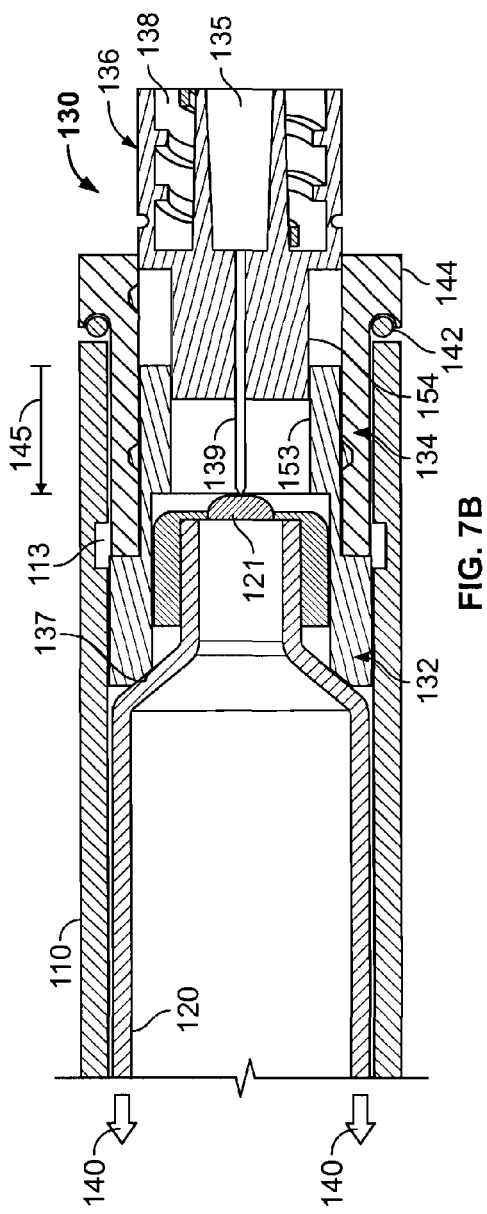
FIG. 7A
FIG. 7B

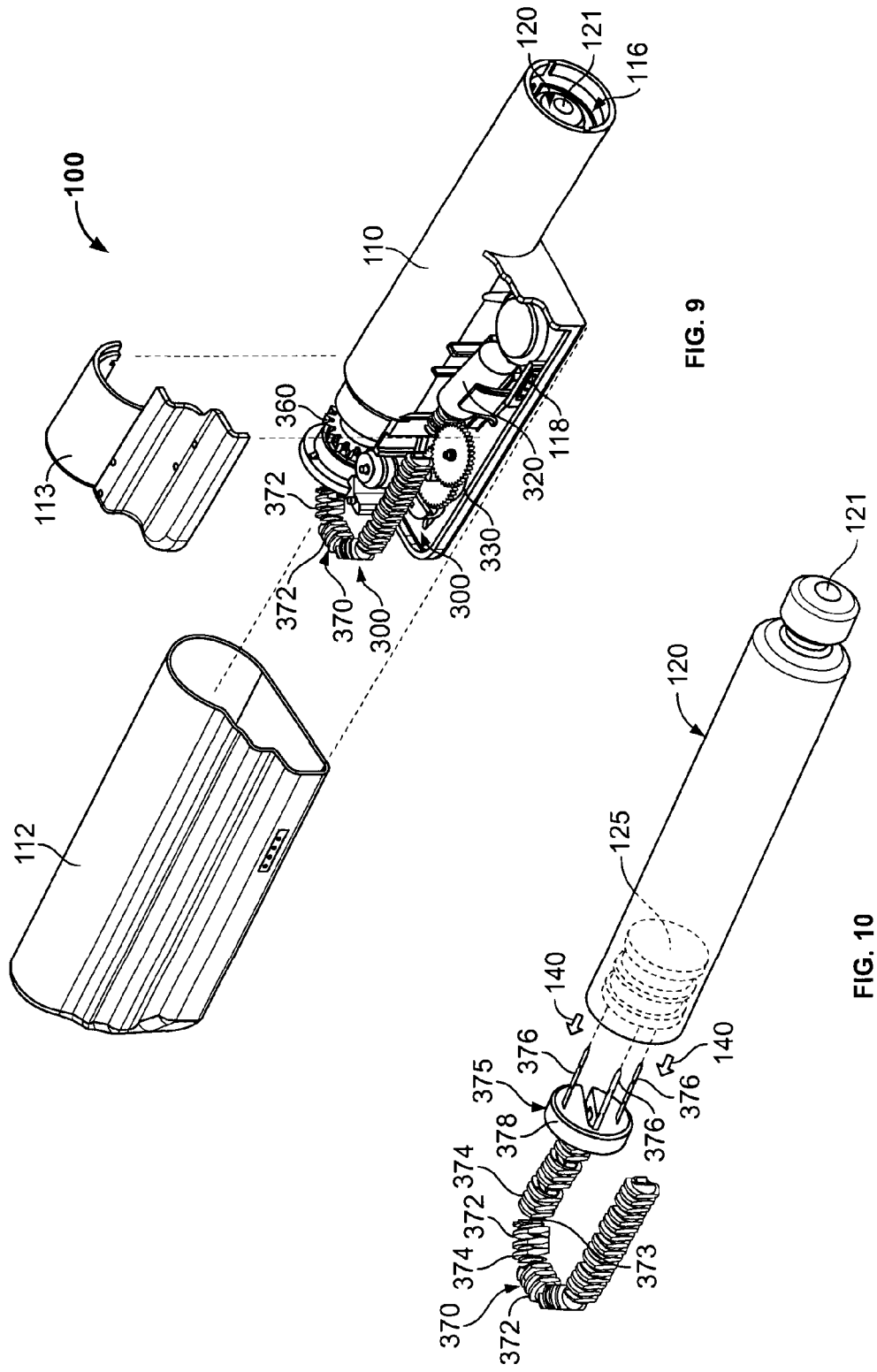

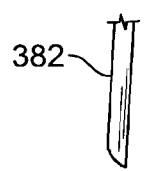
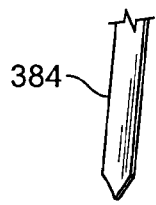
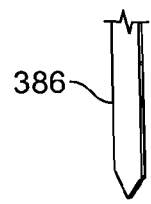
FIG. 14A  FIG. 15A  FIG. 16A
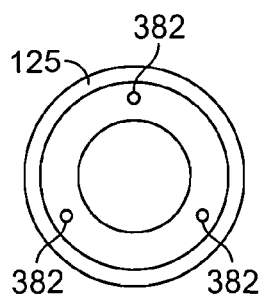
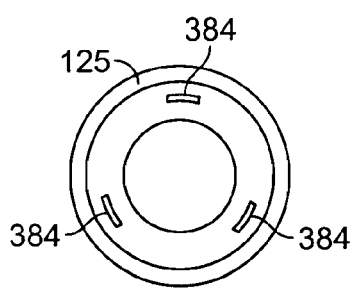
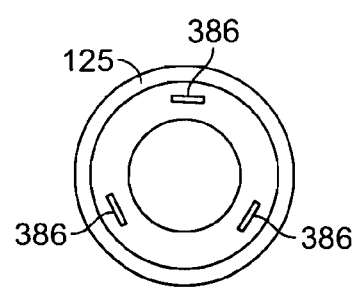
FIG. 14B  FIG. 15B  FIG. 16B
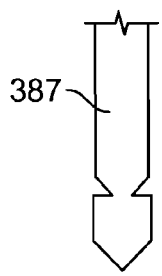
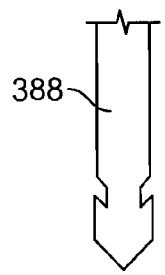
FIG. 17  FIG. 18

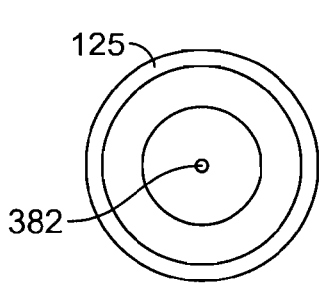
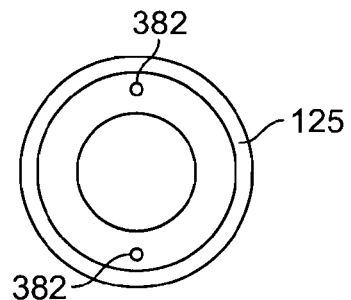
FIG. 19  FIG. 20
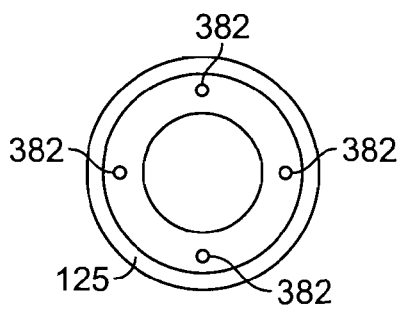
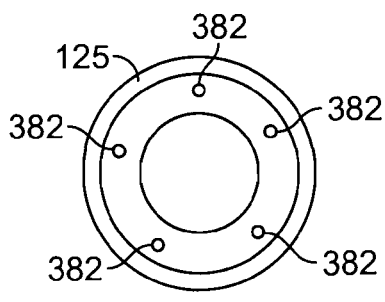
FIG. 21  FIG. 22
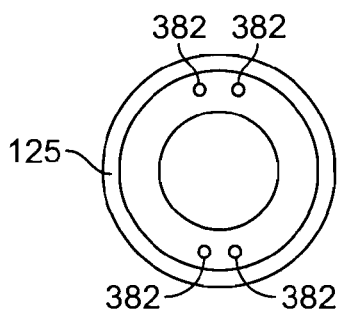
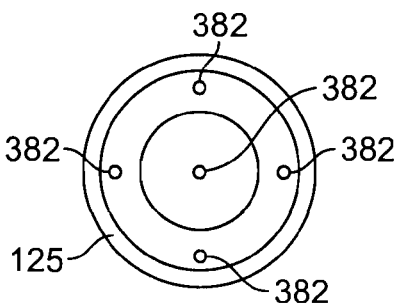
FIG. 23  FIG. 24
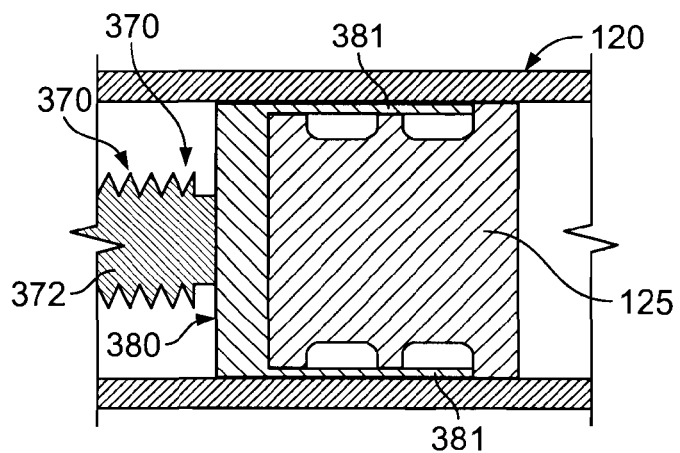
FIG. 25

DISPENSING FLUID FROM AN INFUSION PUMP SYSTEM

TECHNICAL FIELD

This document relates to an infusion pump system, such as a medical infusion pump system.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels.

A number of factors may affect the design of infusion pump devices. One such factor is the size of the device. The pump device may be sized to house the various pump components, yet a large device may reduce the portability for the user. Another factor that may affect the design of an infusion pump device is the reservoir that contains the medicine. For example, if the reservoir is provided in a sealed form, the seal may require penetration before the medicine is infused to the user. Yet another factor that can affect the design of the pump device is the disposability. If, for example, the pump device is to be disposed after exhaustion (e.g., after a single use or a certain number of uses, after a particular period of time, or the like), reuse of the exhausted pump device may create a safety risk to the user.

SUMMARY

Some embodiments of a medical infusion pump system include a pump device having a cap device that mates with a pump housing to retain a medicine cartridge therein. In addition to retaining the medicine cartridge in the pump housing, the cap device may perform one or more functions, such as forcing the medicine cartridge to secure to a pump drive component, piercing a sealed end of the medicine cartridge to provide a flow path for the medicine, priming the plunger in the medicine cartridge with a "break away" force, providing a flow sensor to the medicine flow path, locking the medicine cartridge in the pump housing to promote disposal of the pump device after the medicine cartridge is exhausted, preventing the dispensation of medicine if the cap device is improperly engaged with the pump housing, or a combination thereof.

In addition or in the alternative, some embodiments of the pump device may include a drive system that reliably advances a piston rod to dispense medicine to the patient. The drive system may employ a spring device or the like to provide the dispensing drive energy to a ratchet mechanism. Also, the drive system may include an electrically powered actuator (e.g., a reversible motor) that provides the reset energy to the ratchet mechanism yet contributes no force on the ratchet mechanism when the spring device is delivering the dispensing drive energy. In such circumstances, the pump device can reliably and accurately dispense dosages of medicine in a safe and energy efficient manner.

In some embodiments, an infusion pump device may include a pump housing that defines a space to receive a medicine. The infusion pump device may also include a drive system to dispense a medicine from the pump housing when the medicine is received in the space. The drive system may include a ratchet mechanism that advances a piston rod during a drive step to dispense the medicine when the medicine is received in the space. Also, the drive system may include an electrically powered actuator that decouples from the ratchet mechanism during the drive step.

Particular embodiments of an infusion pump device may include a pump housing that defines a space to receive a medicine. The infusion pump device may also include a drive system to dispense a medicine from the pump housing when the medicine is received in the space. The drive system may include a drive wheel that rotates to advance a piston rod toward the medicine to dispense the medicine when the medicine is received in the space. The drive system may further include a ratchet wheel that is incrementally rotated in a forward direction to rotate the drive wheel and thereby advance the piston rod. The drive system may also include a movable pawl that engages the ratchet wheel. The movable pawl may be adjustable from a reset position to a forward position so as to incrementally rotate the ratchet wheel in the forward direction. The drive system may further include a spring device that urges the movable pawl to adjust from the reset position to the forward position. Also, the drive system may include an actuator assembly that acts upon the movable pawl to force the movable pawl to the reset position and that reverses to separate from the movable pawl when the spring device adjusts the movable pawl from the reset position to the forward position.

Some embodiments may include a method of dispensing medicine from an infusion pump device. The method may include resetting a ratchet mechanism in a drive system of an infusion pump device by activating an electrically powered actuator to provide a reset force to a ratchet mechanism. The method may further include driving the ratchet mechanism in a forward direction to advance a piston rod during a drive step so as to dispense a medicine from the infusion pump device. The electrically powered actuator may be decoupled from the ratchet mechanism during the drive step.

Some or all of the embodiments may provide one or more of the following advantages. First, the pump device may be attached to a controller device so that a user can readily monitor infusion pump operation by simply viewing a user interface connected to the pump device. In these circumstances, the user may activate and control the pump device without the requirement of locating and operating a separate monitoring module.

Second, the infusion pump system may be configured to be portable, wearable, and (in some circumstances) concealable. For example, a user can conveniently wear the infusion pump system on the user's skin under clothing or can carry the pump device in the user's pocket (or other portable location) while receiving the medicine dispensed from the pump device.

Third, a number of preparatory functions can be accomplished while the user performs the relatively simple task of attaching the cap device to the pump housing. For example, attachment of the cap device can cause the medicine cartridge to be retained in a cavity of the pump housing and can provide a water-tight seal for cavity. In another example, attachment of the cap device can force the plunger of the medicine cartridge to secure to the piston rod in the pump device. In a further example, attachment of the cap device can cause a sealed end of the medicine cartridge to be pierced and thereby provide a flow path for the medicine. In another example, attachment of the cap device can provide a "break away" force to initiate movement of the plunger in the medicine cartridge.

Fourth, one or more of safety functions can be performed while the user performs the task of attaching the cap device to the pump housing. For example, attachment of the cap device may arrange a flow sensor in the medicine flow path to detect occlusions. In another example, attachment of the cap device may result in the medicine cartridge being locked in the pump housing. Such a configuration may be useful, for example, in circumstances in which the pump device is designed to be a "one time use" disposable unit. In a further example, if the cap device is improperly engaged with the pump housing, the dispensation of medicine can be prevented.

Fifth, some embodiments of the drive system of the pump device can accurately and incrementally dispense fluid from the pump device in a controlled manner.

Sixth, the drive system of the pump device can be controlled dispense dosages of medicine in a safe and energy efficient manner. For example, in some embodiments, the motor of the drive system can be decoupled from the ratchet mechanism during the drive step. In such a configuration, the motor is not required to draw energy from a battery over an extended period of time (e.g., during the drive step in which the piston rod is advanced to dispense medicine over a period of time).

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3 is an perspective exploded view of a portion of the infusion pump system of FIG. 1.

FIG. 4 is a perspective exploded view of a cap device of the infusion pump system of FIG. 1, in accordance with some embodiments.

FIG. 5 is a perspective exploded view of the cap device of FIG. 4.

FIG. 6 is a perspective exploded view of the cap device of FIG. 4.

FIGS. 7A-D are cross-sectional views of a portion of the infusion pump system of FIG. 1, in accordance with some embodiments.

FIG. 9 is an exploded perspective view of a portion of a pump device of the infusion pump system of FIG. 1, in accordance with some embodiments.

FIG. 10 is an exploded perspective view of a piston rod and a medicine cartridge plunger of the pump device of FIG. 9.

FIGS. 14A-B are perspective and axial views of a plunger penetration member and a medicine cartridge plunger, in accordance with some embodiments.

FIGS. 15A-B are perspective and axial views of a plunger penetration member and a medicine cartridge plunger, in accordance with other embodiments.

FIGS. 16A-B are perspective and axial views of a plunger penetration member and a medicine cartridge plunger, in accordance with further embodiments.

FIG. 17 is a side view of a plunger penetration member having a retention portion, in accordance with some embodiments.

FIG. 18 is a side view of a plunger penetration member having a retention portion, in accordance with some embodiments.

FIG. 19 is an axial view of a plunger penetration member and a medicine cartridge plunger, in accordance with particular embodiments.

FIG. 20 is an axial view of plunger penetration members and a medicine cartridge plunger, in accordance with other embodiments.

FIG. 21 is an axial view of plunger penetration members and a medicine cartridge plunger, in accordance with some embodiments.

FIG. 22 is an axial view of plunger penetration members and a medicine cartridge plunger, in accordance with particular embodiments.

FIG. 23 is an axial view of plunger penetration members and a medicine cartridge plunger, in accordance with other embodiments.

FIG. 24 is an axial view of plunger penetration members and a medicine cartridge plunger, in accordance with some embodiments.

FIG. 25 is cross-sectional side view of plunger engagement device of a piston rod and a medicine cartridge plunger, in accordance with some embodiments.

Like reference symbols in the various drawings indicate like elements.

DETAILED DESCRIPTION OF ILLUSTRATIVE EMBODIMENTS

Figure 1:
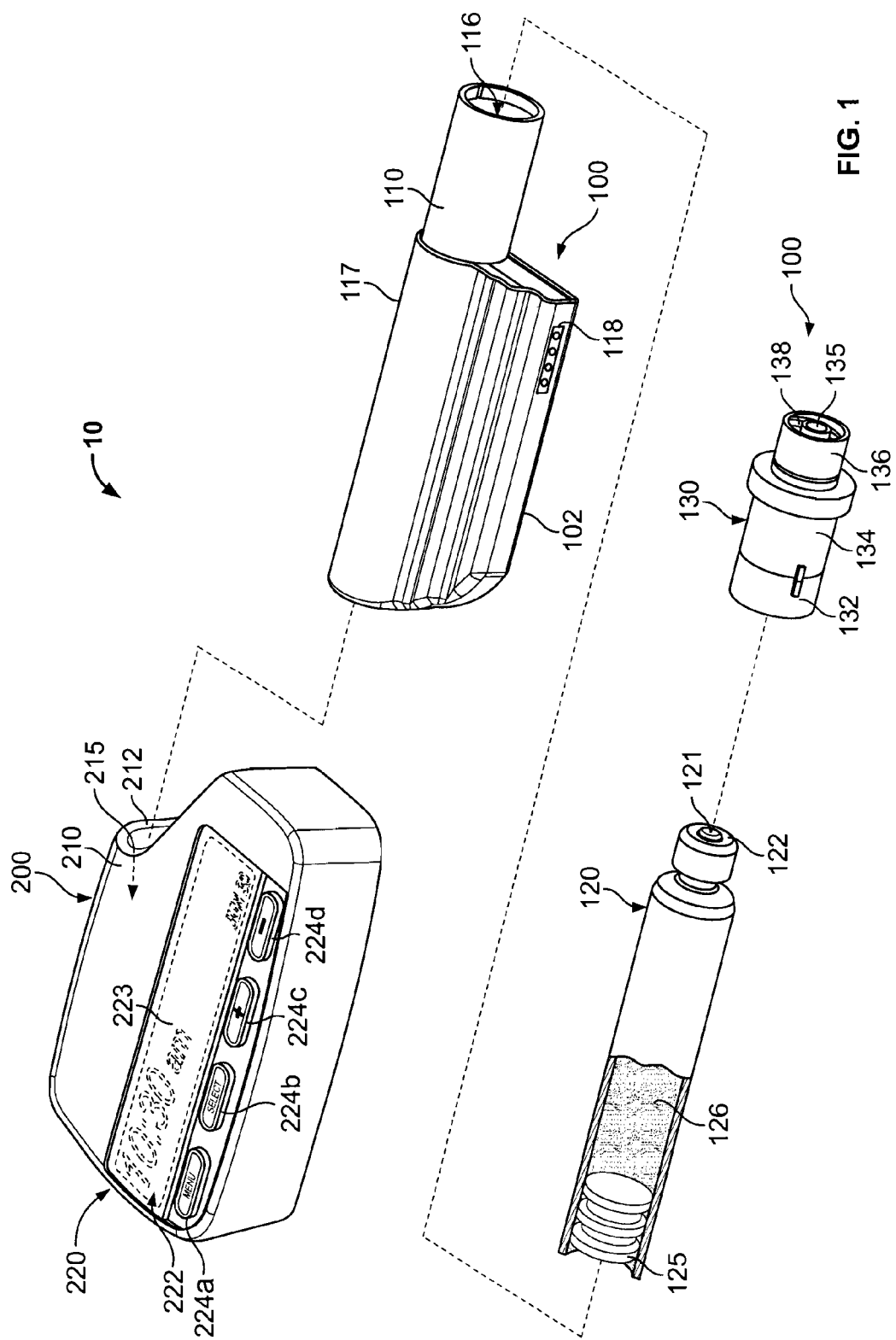
FIG. 1 is a perspective exploded view of an infusion pump system in accordance with some embodiments.

Referring to FIG. 1, an infusion pump system 10 can include a pump device 100 and a controller device 200 that communicates with the pump device 100. The pump device 100 includes a housing structure 110 that defines a cavity 116 in which a fluid cartridge 120 can be received. The pump device 100 also includes a cap device 130 to retain the fluid cartridge 120 in the cavity 116 of the housing structure 110. The pump device 100 includes a drive system (described in more detail below) that advances a plunger 125 in the fluid cartridge 120 so as to dispense fluid therefrom. The controller device 200 communicates with the pump device 100 to control the operation of the drive system. When the controller device 200, the pump device 100 (including the cap device 130), and the fluid cartridge 120 are assembled together, the user can (in some embodiments) conveniently wear the infusion pump system 10 on the user's skin under clothing or in the user's pocket while receiving the fluid dispensed from the pump device 100.

The controller device 200 may be configured as a reusable component that provides electronics and a user interface to control the operation of the pump device 100. In such circumstances, the pump device 100 can be a disposable component that is disposed of after a single use. For example, the pump device 100 can be a "one time use" component that is thrown away after the fluid cartridge 120 therein is exhausted. Thereafter, the user can removably attach a new pump device 100 to the reusable controller device 200 for the dispensation of fluid from a new fluid cartridge 120. Accordingly, the user is permitted to reuse the controller device 200 (which may include complex or valuable electronics) while disposing of the relatively low-cost pump device 100 after each use. Such a pump system 10 can provide enhanced user safety as a new pump device 100 (and drive system therein) is employed with each new fluid cartridge 120.

In use, the cap device 130 is coupled to the pump housing 110 to retain the fluid cartridge 120 in the cavity 116 of the pump device 100, and the pump device 100 (with the fluid cartridge therein) is removably attached to the controller device 200. The cap device 130 may be multifunctional in that it performs a number of functions for the pump device operation. For example, in some embodiments, attachment of the cap device 130 may cause one or more of the following preparatory functions: forcing the plunger 125 of the fluid cartridge 120 to secure to a piston rod (described in connection with FIG. 7B), piercing a septum 121 of the fluid cartridge 120 to provide a flow path for the fluid (described in connection with FIG. 7C), and priming the fluid cartridge 120 with a "break away" force to initiate movement of the plunger 125 in the fluid cartridge 120 (described in connection with FIG. 7D). In addition or in the alternative, attachment of the cap device 130 may also cause one or more of the following safety related functions: aligning a flow sensor with the fluid flow path (described in connection with FIGS. 8A-B), locking the fluid cartridge 120 in the pump housing 110 to thereby promote disposal of the pump device 100 after exhaustion (described in connection with FIGS. 8A-B), and ceasing or preventing the dispensation of fluid if the cap device 130 is improperly engaged with the pump housing 110 (described in connection with FIGS. 8A-B).

In addition, the drive system of the pump device 100 may have a design that enables the dispensing of fluid in a safe and energy efficient manner. As described in more detail below in connection with FIGS. 26-30, the piston rod can be advanced incrementally using pawl and ratchet techniques. For each incremental advancement of the piston rod, there is a reset step and a drive step. In the reset step, an electrically powered component forces a pawl to move in a first direction and to engage another tooth of a ratchet wheel. Then, when the pawl is engaged on the next tooth of the ratchet wheel, the drive step begins in which the electrically powered component decouples from the pawl (e.g., the electrically powered actuator assembly separates from the pawl). This allows a spring device that is attached to the pawl to move the pawl in the opposite direction, thereby causing the ratchet wheel to turn an incremental amount. A gear system translates the incremental rotation of the ratchet wheel into incremental advancement of the piston rod. Among other advantages, such embodiments of the drive system help to reduce the overall time that the electrical power is drawn from a battery, which may facilitate a reduction in battery requirements. In addition, the release of medicine from the cartridge, which occurs during the drive step, is caused only by the force applied by the spring, and thus is consistent and repeatable. Examples of such drive systems are described in more detail below in connection with FIGS. 26-30.

Still referring to FIG. 1, in this embodiment, the pump system 10 is a medical infusion pump system that is configured to controllably dispense a medicine from the cartridge 120. As such, the fluid cartridge 120 may contain a medicine 126 to be infused into the tissue or vasculature of a targeted individual, such as a human or animal patient. For example, the pump device 100 can be adapted to receive a medicine cartridge 120 in the form of a carpule that is preloaded with insulin or another medicine for use in the treatment of Diabetes (e.g., Byetta®, Symlin®, or others). Such a cartridge 120 may be supplied, for example, by Eli Lilly and Co. of Indianapolis, Ind. Other examples of medicines contained in the fluid cartridge 120 include: pain relief drugs, hormone therapy, blood pressure treatments, anti-emetics, osteoporosis treatments, or other injectable medicines. The fluid cartridge 120 may have other configurations. For example, the pump housing structure 110 may include one or more walls that surround a plunger to define a reservoir in which the medicine is injected or otherwise received.

In some embodiments, the controller device 200 may be removably attached to the pump device 100 so that the two components are mechanically mounted to one another in a fixed relationship. Such a mechanical mounting can form an electrical connection between the removable controller device 200 and the pump device 100. For example, the controller device 200 may be in electrical communication with a portion of a drive system (not shown in FIG. 1) of the pump device 100. As described in more detail below, the pump device 100 includes a drive system that causes controlled dispensation of the medicine or other fluid from the cartridge 120. In some embodiments, the drive system incrementally advances a piston rod (not shown in FIG. 1) longitudinally into the cartridge 120 so that the fluid is forced out of an output end 122. A septum 121 at the output end 122 of the fluid cartridge 122 can be pierced to permit fluid outflow when the cap device 130 is connected to the pump housing structure 110 (described in more detail below). Thus, when the pump device 100 and the controller device 200 are attached and thereby electrically connected, the controller device 200 communicates electronic control signals via a hard-wire-connection (e.g., electrical contacts or the like) to the drive system or other components of the pump device 100. In response to the electrical control signals from the controller device 200, the drive system of the pump device 100 causes medicine to incrementally dispense from the medicine cartridge 120.

Still referring to FIG. 1, the controller device 200 includes a controller housing structure 210 that is configured to mate with a complementary portion of the pump housing structure 110 so as to form a releasable mechanical connection. For example, the controller housing structure 210 may define a cavity 215 that mates with a portion of the pump housing structure 110 for a snap fit engagement (as shown, for example, in FIG. 2). Also, the controller housing structure 210 may include a tab 212 that engages a mating surface 117 of the pump housing structure 110 when the controller device 200 is removably attached to the pump device 100. In some embodiments, a magnetic attachment may be employed to releasably secure the pump device 100 to the controller device 200. For example, the magnetic attachment can serve to retain the pump housing structure 110 in the cavity 215 defined by the controller housing structure 210. In alternative embodiments, one or more releasable connector devices (e.g., mating tongues and grooves, mounting protrusions friction fit into mating cavities, or the like) can be used to further implement the releasable attachment of the controller device 200 to the pump device 100.

As shown in FIG. 1, the pump device 100 may include one or more electrical contacts 118 (e.g., conductive pads, pins, and the like) that are exposed to the controller device 200 and that mate with complementary electrical contacts (not show in FIG. 1) on the adjacent face of the controller device 200. The electrical contacts 118 provide the electrical communication between the control circuitry (e.g., one or more circuits including a microprocessor or the like and memory) housed in the controller device 200 and at least a portion of the drive system or other components of the pump device 100. For example, in some embodiments, the electrical contacts permit the transmission of electrical control signals to the pump device 100 and the reception of feedback signals (e.g., sensor signals) from particular components within the pump device 100. Previously filed U.S. patent application Ser. No. 11/522,603 (incorporated herein by reference) describes further embodiments of a controller device that can be attached to and communicate with a pump device.

Still referring to FIG. 1, the controller device 200 includes a user interface 220 that permits a user to monitor the operation of the pump device 100. In some embodiments, the user interface includes a display 222 and one or more user-selectable buttons (e.g., four buttons 224a, 224b, 224c, and 224d in this embodiment). The display 222 may include an active area 223 in which numerals, text, symbols, images, or combination thereof can be displayed. For example, the display 222 may be used to communicate a number of settings or menu options for the infusion pump system 10. In this embodiment, the user may press one or more of the buttons 224a, 224b, 224c, and 224d to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). In some embodiments, the user can adjust the settings or otherwise program the controller device 200 by pressing one or more buttons 224a, 224b, 224c, and 224d of the user interface 220. For example, in embodiments of the infusion pump system 10 configured to dispense insulin, the user may press one or more of the buttons 224a, 224b, 224c, and 224d to change the dispensation rate of insulin or to request that a bolus of insulin be dispensed immediately or at a scheduled, later time.

The display 222 of the user interface 220 may be configured to display quick reference information when no buttons 224a, 224b, 224c, and 224d have been pressed. In this example, the active area 223 of the display 222 can display the time and the date for a period of time after no button 224a, 224b, 224c, and 224d has been actuated (e.g., five seconds, 10 seconds, 30 seconds, 1 minute, 5 minutes, or the like). Thereafter, the display 222 may enter sleep mode in which the active area 223 is blank, thereby conserving battery power. In addition or in the alternative, the active area can display particular device settings, such as the current dispensation rate or the total medicine dispensed, for a period of time after no button 224a, 224b, 224c, or 224d has been actuated (e.g., five seconds, 10 seconds, 30 seconds, 1 minute, 5 minutes, or the like).

Again, thereafter the display 222 may enter sleep mode to conserve battery power. In certain embodiments, the display 222 can dim after a first period of time in which no button 224a, 224b, 224c, or 224d has been actuated (e.g., after 15 seconds or the like), and then the display 22 can enter sleep mode and become blank after a second period of time in which no button 224a, 224b, 224c, or 224d has been actuated (e.g., after 30 seconds or the like). Thus, the dimming of the display device 222 can alert a user viewing the display device 222 when the active area 223 of the display device will soon become blank.

Accordingly, when the controller device 200 is connected to the pump device 100, the user is provided with the opportunity to readily monitor infusion pump operation by simply viewing the user interface 220 connected to the pump device 100. Such monitoring capabilities may provide comfort to a user who may have urgent questions about the current operation of the pump device 100 (e.g., the user may be unable to receive immediate answers if wearing an infusion pump device having no user interface attached thereto).

Also, in these embodiments, there may be no need for the user to carry and operate a separate module to monitor the operation of the infusion pump device 100, thereby simplifying the monitoring process and reducing the number of devices that must be carried by the user. If a need arises in which the user desires to monitor the operation of the pump device 100 or to adjust settings of the pump system 10 (e.g., to request a bolus amount of medicine), the user can readily operate the user interface 220 removably attached to the pump device 100, without the requirement of locating and operating a separate monitoring module.

In other embodiments, the user interface 200 is not limited to the display and buttons depicted in FIG. 1. For example, in some embodiments, the user interface 220 may include only one button or may include a greater numbers of buttons, such as three buttons, four buttons, five buttons, or more. In another example, the user interface 220 of the controller device 200 may include a touch screen so that a user may select buttons defined by the active area of the touch screen display. Alternatively, the user interface 220 may comprise audio inputs or outputs so that a user can monitor the operation of the pump device 100.

Figure 2:
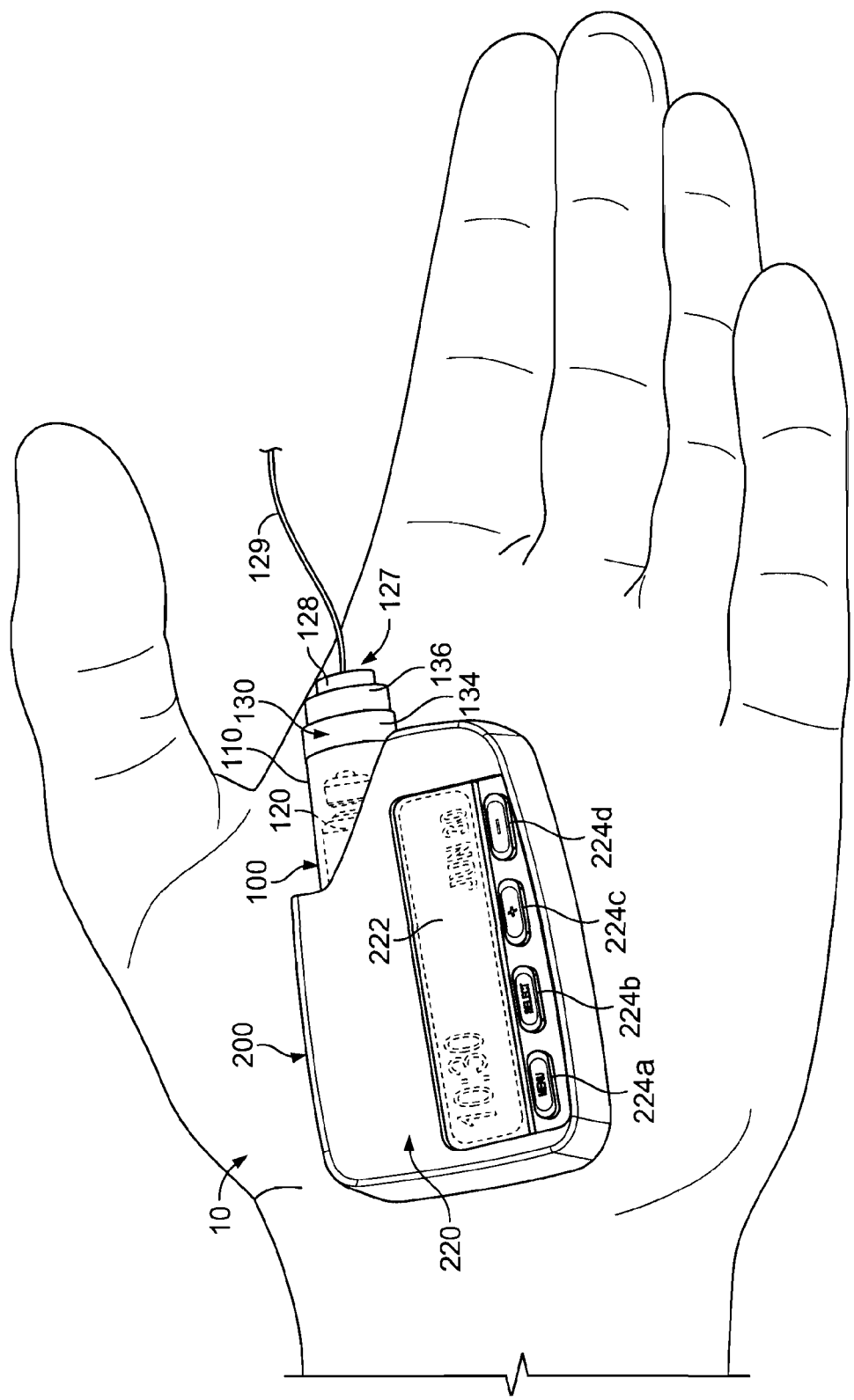
FIG. 2 is a perspective view of the infusion pump system of FIG. 1.

Referring to FIG. 2, the infusion pump system 110 may be configured to be portable and can be wearable and concealable. For example, a user can conveniently wear the infusion pump system 110 on the user's skin (e.g., skin adhesive) underneath the user's clothing or carry the pump device 100 in the user's pocket (or other portable location) while receiving the medicine dispensed from the pump device 100. As described below in connection with FIGS. 26-30, the drive system may be housed in the housing structure 110 of the pump device 100 in a compact manner so that the pump device 100 has a reduced length. For example, in the circumstances in which the medicine cartridge 120 has a length of about 6 cm to about 7 cm (about 6.4 cm in one embodiment), the overall length of the pump housing structure 110 (which contains medicine cartridge and the drive system) can be about 7 cm to about 9 cm (about 8.3 cm or less in one embodiment). In addition, the pump housing structure 110 may have an overall height of about 1.5 cm to about 4 cm (about 2.9 cm or less in one embodiment) and an overall thickness of about 8 mm to about 20 mm (about 14.5 mm or less in one embodiment). In such circumstances, the controller device 200 can be figured to mate with the pump housing 110 so that, when removably attached to one another, the components define a portable infusion pump unit that stores a relatively large quantity of medicine compared to the overall size of the unit. For example, in this embodiment, the infusion pump system 110 (including the pump device 100 attached to the removable controller device 200) may have an overall length of about 7 cm to about 9 cm (about 8.5 cm or less in one embodiment), an overall height of about 1.5 cm to about 4 cm (about 3.5 cm or less in one embodiment), and an overall thickness of about 8 mm to about 20 mm (about 15 mm or less in one embodiment).

The pump system 110 is shown in FIG. 2 as being held in a user's hand so as to illustrate an exemplary size of the system 110. As shown, this embodiment of the infusion pump system 10 is pocket-sized so that the pump device 100 and controller device 200 can be worn in the user's pocket or in another portion of the user's clothing. In such embodiments, the cap device 130 of the pump device 100 may be configured to mate with an infusion set 127. In general, the infusion set 127 is tubing system that connects the infusion pump device 100 to the user (e.g., to deliver medicine into the vasculature under the user's skin). The infusion set 127 may include a connector 128 (e.g., a leur connector), a flexible tube 129 that extends from the connector 128 to a subcutaneous cannula (not shown in FIG. 2), and a skin adhesive patch (not shown in FIG. 2) that secures the subcutaneous cannula to the infusion site. The skin adhesive patch can retain the infusion cannula in fluid communication with the tissue or vasculature of the patient so that the medicine dispensed through the tube 129 passes through the cannula and into the user's body. The cap device 130 may provide fluid communication between the output end 122 (FIG. 1) of the medicine cartridge 120 and the tube 129 of the infusion set 127. In these embodiments, the user can carry the portable infusion pump system 10 (e.g., in the user's pocket, connected to a belt clip, adhered to the user's skin, or the like) while the tube 129 extends to the location in which the skin is penetrated for infusion. If the user desires to monitor the operation of the pump device 100 or to adjust the settings of the infusion pump system 10, the user can readily access the user interface 220 of the controller device 200 without the need for carrying and operating a separate module.

In other embodiments, the infusion pump system 10 may be configured to adhere to the user's skin directly at the location in which the skin is penetrated for medicine infusion. For example, a rear surface 102 (FIG. 1) of the pump device 100 may include a skin adhesive patch so that the pump device 100 is physically adhered to the skin of the user at a particular location. In these embodiments, the cap device 130 may have a configuration in which medicine passes directly from the cap device 130 into an infusion cannula that is penetrated into the user's skin. In one example, the fluid output port through the cap device 130 may include a curve or a 90° corner so that the medicine flow path extends longitudinally out of the medicine cartridge and then laterally toward the patient's skin. Again, if the user desires to monitor the operation of the pump device 100 or to adjust the settings of the infusion pump system 10, the user can readily access the user interface 220 of the controller device 200 without the need for carrying and operating a second, separate device. For example, the user may look toward the pump device 100 to view the user interface 220 of the controller device 220 that is removably attached thereto.

Referring now to FIG. 3, the cap device 130 may include a number of components that permit the cap device 130 to mate with the pump housing 110 and to interact with the medicine cartridge 120. For example, in this embodiment, the cap device comprises a slider component 132, and rotator component 134, and a fluid path component 136 that can be assembled together. The fluid path component 136 may include needle penetrator 139 (shown, for example, in FIG. 4) that is advanced through the septum 121 of the cartridge 120 when the cap device 130 is received by the pump housing 110. The needle penetrator 139 may comprise a hollow needle device that provides fluid communication with an output port 135 of the fluid path component 136. The output port 135 is capable of directing the fluid toward the infusion set tubing 129 (FIG. 2) when the infusion set connector 128 (FIG. 2) is joined with the cap device 130. In this embodiment, the infusion set connector 128 (FIG. 2) is a leur connector that mates with a threaded cavity 138 of the fluid path component 136. As such, the leur connector can be secured into the threaded cavity 138 so that the output port 135 comes into fluid communication with the infusion set tubing 129 (FIG. 2).

Still referring to FIG. 3, one or more components of the cap device 130 may engage the portion of the pump housing 110 that defines the cavity 116 in which the medicine cartridge 120 is received. For example, in this embodiment, the slider component 132 includes a first set of protrusions 131 that slidably mate with longitudinal slots 111 form in the interior wall of the pump housing 110. Likewise, the rotator component 134 includes a second set of protrusions 133 that also slidably mate with the longitudinal slots 111. Accordingly, the cap device 130 can be advanced into the cavity 116 of the pump housing 110 when the protrusions 131 and 133 are aligned with longitudinal slots 111 of the pump housing 110. Such a configuration provides for guidance of the cap device 130 as the cap device is advanced toward the medicine cartridge 120 received in the cavity 116.

After the cap device 130 is advanced into the cavity a particular distance, the second set of protrusions 133 on the rotator component 134 may align with circumferential slots 113 that extend from the longitudinal slots 111. For example, in this embodiment, the cap device 130 can be advanced into the cavity 116 toward the medicine cartridge 120 until a rim 144 of the rotator component 134 reaches the end face of the pump housing 110. At this point, the protrusions 133 on the rotator component 134 align with the circumferential slots 113, thereby permitting the rotator component 134 to rotate relative to the pump housing 110 (e.g., the protrusions 133 can slide circumferentially within the circumferential slots 113). Although the rotator component 134 of the cap device 130 is permitted to rotate relative to the pump housing 110, the protrusions 131 of the slider component 132 remain engaged with the longitudinal slots 111, thereby permitting the slider component to slide in an axial direction relative to the pump housing (but hindering rotation of the slider component 132 relative to the pump housing 110).

As described in more detail below, the relative movement of the components of the cap device 130 (e.g., rotation of the rotator component 134 and longitudinal advancement of the slider component 132) enables a user to perform a number of functions by merely attaching of the cap device 130 to the pump housing 110. For example, such functions may include one or more of the following: forcing the medicine cartridge 120 to secure to a portion of a piston rod 370 (described in connection with FIGS. 7A-D and 10-25), piercing the septum 121 of the medicine cartridge 120 to provide a flow path for the medicine (described in connection with FIGS. 7A-D), priming the medicine cartridge 120 with a "break away" force to initiate movement of the plunger 125 in the medicine cartridge 120 (described in connections with FIGS. 7A-D), providing the a flow sensor 165 to the medicine flow path (described in connection with FIGS. 8A-B), locking the medicine cartridge 120 in the pump housing 110 to thereby promote disposal of the pump device 100 after exhaustion (described in connection with FIGS. 8A-B), and ceasing or preventing the dispensation of medicine if the cap device 130 is improperly engaged with the pump housing 110 (described in connection with FIGS. 8A-B).

Referring now to FIGS. 4-6, the cap device 130 can be assembled to permit relative movement of the components 132, 134, and 136. In this embodiment, the slider component 132, the rotator component 134 and the fluid path component 136 are assembled to one another along a longitudinal axis 150. The slider component 132 is configured to rotatably engage the rotator component 134. For example, in this embodiment, the slider component 132 includes external cylindrical surfaces 151 that mate with an internal bore 152 of the rotator component 134. As such, the rotator component 134 can rotate relative to the slider component 132.

In addition, the slider component 132 is configured to slidably engage the fluid path component 136. For example, in this embodiment, the slider component 132 includes opposing flat surfaces 153 that mate with complementary flat surfaces 154 of the fluid path component 136. This configuration permits the fluid path component 136 to move longitudinally along the axis 150 toward the slider component 132. When the shoulder surfaces 156 of the fluid path component 136 abut against the forward faces 155 of the slider component 132, the longitudinal movement of the fluid path component 136 can cause similar movement of the slider component 132. Also, this configuration permits the fluid path component 136 to remain rotationally fixed relative to the slider component 132. For example, the fluid path component 136 remains rotationally stationary when the slider component 132 is retained in a rotationally stationary position (e.g., when the slider component protrusions 131 are mated with the longitudinal slots 111 of the pump housing 110 (FIG. 3)). As such, the slider component 132 and the fluid path component 136 can remain rotationally stationary relative to the pump housing 110 (FIG. 3) while the rotator component 134 is rotated relative to the pump housing 110.

Still referring to FIGS. 4-6, the rotator component 134 may be configured to engage the fluid path component 136 such that rotational movement of the rotator component 134 causes longitudinal movement of the fluid path component 136. For example, in this embodiment, the rotator component 134 includes an internal thread pattern 157 that mates with an external thread pattern 158 of the fluid path component 136. The thread patterns 157 and 158 mate together when the slider component 132 and the fluid path component 136 are arranged at least partially in the rotator component 134. Accordingly, when the slider component 132 is retained in a rotationally stationary position (e.g., when the slider component protrusions 131 are mated with the longitudinal slots 111 of the pump housing 110 (FIG. 3)), the rotator component 134 can rotate relative thereto and thereby cause the longitudinal movement of the fluid path component 136. In these circumstances, the engagement of the flat surfaces 153 with the complementary flat surfaces 154 prevents the fluid path component 136 from rotating with the rotator component 134, so the thread engagement translates the rotator component's rotational movement to the fluid path component's longitudinal movement.

As previously described, the fluid path component 136 includes a needle penetrator 139 that extends longitudinally to pierce the septum 121 of the medicine cartridge 120 (FIG. 3) when the cap device 130 is urged toward the medicine cartridge 120. The needle penetrator 139 of the fluid path component 136 is configured to extend through a bore 159 (FIGS. 4-6) of the slider component 132 when the cap device 130 is assembled. As such, during engagement of the cap device 130 with the pump housing 110 (FIG. 3), the cap device 130 can be operated to penetrate the medicine cartridge 120 and create a fluid path to the output port 135. As described in more detail below, the cap device 130 may also be used to perform a number of other functions when the user performs the relatively simple task of engaging the cap device 130 to the pump housing 110.

Referring now to FIGS. 7A-D and 8A-B, some embodiments of the cap device 130 are capable of performing multiple functions when the cap device 130 is being coupled to the pump housing 110. Some of these functions may include preparatory functions and safety functions. For example, in some embodiments, attachment of the cap device 130 may cause one or more of the following preparatory functions: retaining the medicine cartridge 120 in the cavity 116 of the pump housing 110 (described in connection with FIG. 7A), forcing the plunger 125 of the medicine cartridge 120 to secure to a piston rod (described in connection with FIG. 7B), piercing the septum 121 of the medicine cartridge 120 to provide a flow path for the medicine (described in connection with FIG. 7C), and priming the medicine cartridge 120 with a "break away" force to initiate movement of the plunger 125 in the medicine cartridge 120 (described in connection with FIG. 7D). In addition or in the alternative, attachment of the cap device 130 may also cause one or more of the following safety related functions: aligning a flow sensor 165 with the medicine flow path (described in connection with FIGS. 8A-B), locking the medicine cartridge 120 in the pump housing 110 to thereby promote disposal of the pump device 100 after exhaustion (described in connection with FIGS. 8A-B), and ceasing or preventing the dispensation of medicine if the cap device 130 is improperly engaged with the pump housing 110 (described in connection with FIGS. 8A-B).

Referring to now FIG. 7A, the cap device 130 can be coupled to the pump device 100 so as to retain the medicine cartridge 120 in the cavity 116 of the pump housing 110. In this embodiment, the medicine cartridge 120 includes a cylindrical wall that fits within the cylindrical cavity 116 at least partially defined by the pump housing 110. As shown in FIG. 7A, the cap device 130 may approach the pump housing 110 after the medicine cartridge 120 is received in the cavity 116 so that the cap device 130 seals the cavity 116 and retains the cartridge 120 therein. For example, the rim 144 of the cap device 130 may include a seal 142 (e.g., an elastomer o-ring seal or the like) that provides a water-tight seal when the rim 144 is urged against the front face of the pump housing 110. The cartridge may be arranged the pump housing 110 so that the septum 121 at the output end 122 faces toward the cap device 130 when the cap device 130 engages the pump housing 110. As such, the plunger 125 of the medicine cartridge 120 is arranged in the cavity 116 to face toward a component of the pump drive system, such as a piston rod 370 (as described in more detail below, for example, in connection with FIGS. 9-10). In this embodiment, the medicine cartridge 120 comprises an insulin carpule that is separate from the pump device 100. In such circumstances, the medicine cartridge 120 may be inserted into the cavity 116 to rest against a portion of the piston rod 370 (FIG. 10).

Referring to FIG. 7B, during engagement of the cap device 130 to the pump housing 110, a longitudinal force 140 may be applied to the medicine cartridge 120 so a portion of the medicine cartridge 120 becomes secured to the piston rod 370 (e.g., the plunger 125 becomes secured to a plunger engagement device 375 of the piston rod 370 as shown in FIG. 10). This longitudinal force 140 may be applied to the medicine cartridge 120 when at least a portion of the cap device 130 is inserted under force from a user into the pump housing 110. For example, in this embodiment, the slider component 132 of the cap device 130 includes the first set of protrusions 131 (FIG. 3) that mate with the longitudinal slots 111 (FIG. 7A) of the pump housing 110 during the guided insertion of the cap device 130 into the cavity 116. During this insertion, the slide component 132 includes a shoulder surface 137 that abuts with the medicine cartridge 120. The insertion force applied by the user during the attachment of the cap device 130 to the pump housing 110 can be translated to a longitudinal force 140. As described in more detail below in connection with FIGS. 9-10, this longitudinal force 140 can be used to secure the medicine cartridge 120 to the piston rod 370 or to another component of the drive system. For example, during the attachment of the cap device 130 to the pump housing 110, the slider component 132 may act upon the medicine cartridge 120 to force the medicine cartridge 120 a rearward displacement 145 that drives the plunger 125 (FIG. 10) toward one or more penetration members 376 of the plunger engagement device 375 of the piston rod 370. In such circumstances, the penetration members 376 (FIG. 10) penetrate into the plunger 125 of the medicine cartridge 120 and thereby secure the medicine cartridge 120 the piston rod 370 (FIG. 10). A number of further embodiments for the plunger engagement device are described in more detail below in connection with FIGS. 9-25.

Figure 7C:
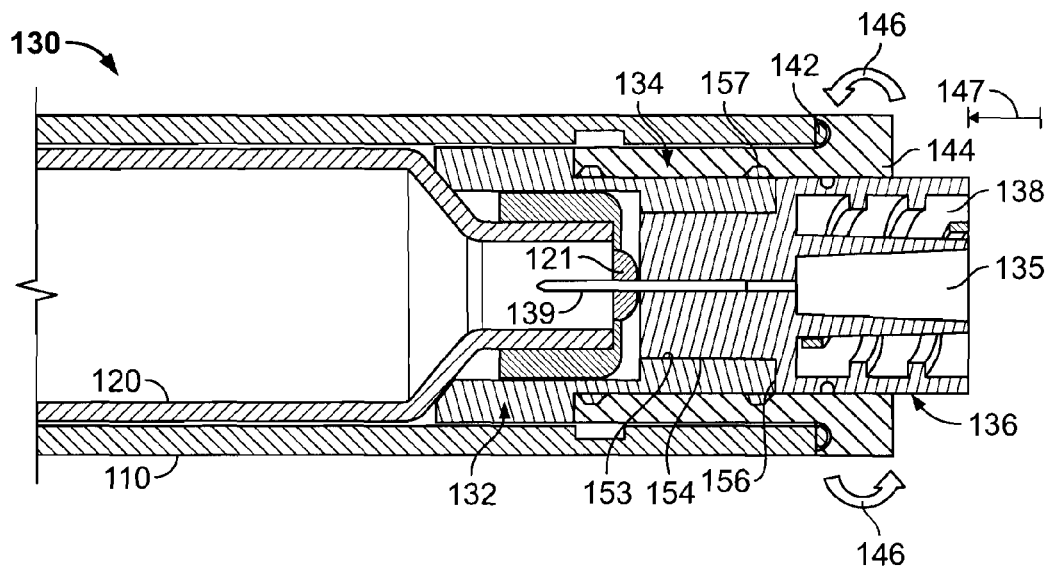

Referring to FIG. 7C, when the cap device 130 is inserted longitudinally into the cavity 116 to a particular depth, the rim 144 and the seal 142 can be urged against the end face of the pump housing 110 to seal the medicine cartridge 120 in the cavity 116. Also, as previously described in connection with FIG. 3, the second set of protrusions 133 on the rotator component 134 may align with the circumferential slots 113 in the pump housing 110 when the cap device 130 is inserted to this particular depth. As such, the rotator component 134 of the cap device 130 is rotatable relative to the pump housing 110 (e.g., the protrusions 133 can move circumferentially in the circumferential slots 113). Again, as previously described in connection with FIG. 3, the first protrusions 131 of the slider component 132 remain in the longitudinal slots 111 of the pump housing 110, so the slider component 132 does not rotate with the rotator component 134. Such relative movement between the rotator component 134 and the slider component 132 can be used to longitudinally advance the fluid path component 136 (and its needle penetrator 139) toward the septum 121 of the medicine cartridge 120.

As shown in FIG. 7C, the rotator component 134 of the cap device 130 can be moved in a rotational direction 146 relative to the pump housing 110 (which maintains the slider component 132 in a rotational stationary position due to the engagement of the first protrusions 131 (FIG. 3) and the longitudinal slots 111 (FIGS. 3 and 7A)). For example, a user may grasp the rim 144 of the rotator component 134 and twist it relative to the pump housing 110 so that the second protrusions 133 (FIG. 3) are guided in the circumferential slots 113 (FIG. 3). Such rotation of the rotator component 134 causes the interior thread pattern 157 of the rotator component 134 to engage the exterior thread pattern 158 (not shown in FIG. 7C; refer to FIGS. 4-6) of the fluid path component 136. Because the opposing flat surfaces 153 of the slider component 132 engage the complementary flat surfaces 154 of the fluid path component 136, the fluid path component 136 remains in a rotationally stationary position with the slider component 132 (e.g., the rotator component 134 also rotates relative to the fluid path component 136). As such, the engagement between the thread patterns 157 (on the rotator component 134) and 158 (on the fluid path component 136) cause the rotational motion of the rotator component 134 to be translated into a longitudinal motion for the fluid path component 136. As shown in FIG. 7C, the rotation of the rotator component 134 can cause the fluid path component 136 to move a longitudinal displacement 147 toward the medicine cartridge 120. This longitudinal displacement 147 results in the needle penetrator 139 piercing the septum 121 of the medicine cartridge 120 and thereby establishing a fluid path from the medicine cartridge 120 to the output port 135 of the fluid path component 136.

In some embodiments in which the attachment of the cap device 130 provides the force 140 (FIG. 7B) to cause securement of the medicine cartridge 120 to the piston rod 370 (FIG. 10), this force 140 may be applied before the needle penetrator 139 penetrates the septum 121 (FIG. 7C). Because the septum 121 is not yet pierced during the application of the force 140 (FIG. 7B), the force 140 can be used to urge the plunger 125 against the plunger engagement device 375 (FIG. 10) without necessarily forcing some portion of the medicine out of the cartridge 120.

Figure 7D:
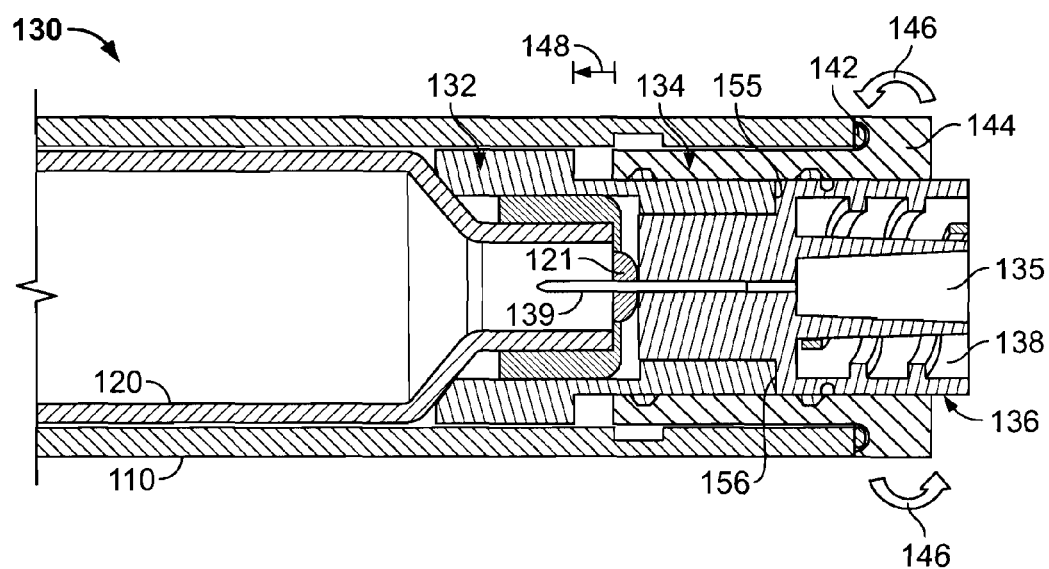

Referring now to FIG. 7D, attachment of the cap device 130 to the pump housing 110 can also provide a "break away" force to initiate movement of the plunger 125 in the medicine cartridge 120. Such a "break away" force may be used prepare the plunger 125 for future incremental displacements caused by the drive system. For example, as shown in FIG. 1, the plunger 125 is arranged in the medicine cartridge 120 as to act upon the medicine 126 therein. The "break away" force that is required to initially move the plunger 125 for the first time may be substantially greater than the operational drive force required to advance the plunger 125 yet another increment toward the output end 122 of the medicine cartridge 120. In this embodiment, the "break away" force can be provided during the attachment of the cap device 130 to the pump body 110, (rather than by activating the drive system to initiate movement of the plunger 125 for the first time). Accordingly, drive system can provide the operational drive force that (during normal operation) advances the plunger 125 in subsequent increments toward the output end 122 of the medicine cartridge 120, and the user's action (during attachment of the cap device 130) can provide the generally greater "break away" force to initiate movement of the plunger 125 for the first time.

Still referring to FIG. 7D, the rotator component 134 of the cap device 130 can be moved in the rotational direction 146 relative to the pump housing 110, for example, by twisting the rim 144 relative to the pump housing 110. As previously described in connection with FIG. 7C, such rotation of the rotator component 134 can be translated into a longitudinal motion for the fluid path component 136. After a particular amount of longitudinal advancement of the fluid path component 136, the shoulder surfaces 156 of the fluid path component 136 abut against the forward faces 155 of the slider component 132 (refer also to FIGS. 4-6). Accordingly, the continued longitudinal movement of the fluid path component 136 (due to the rotation 146 of the rotator component 134) further causes a longitudinal displacement 148 of the slider component 132. As previously described in connection with FIG. 7B, the slider component 132 includes a shoulder surface 137 that acts upon the medicine cartridge 120, so the longitudinal displacement 148 of the slider component 132 causes the medicine cartridge 120 to likewise move in the rearward longitudinal direction. Because the plunger 125 (FIG. 10) is already engaged with the piston rod 370 (FIG. 10) as previously described in connection with FIG. 7B, the plunger 125 does not share in this rearward longitudinal movement. Instead, a break away force 149 is applied to the medicine cartridge 120 relative to the plunger 125 (which is maintained in its position due to the piston rod engagement), thereby causing the initial movement of the plunger 125 in the medicine cartridge 120 for the first time.

It should be understood from the description herein that this initial break away movement of the plunger 125 in the medicine cartridge 120 may cause a small amount of medicine to be dispensed. However, the infusion set connector 128 (FIG. 2) can be joined with the threaded cavity 138 of the fluid path component 136 before the break away force 149 is applied and (in some embodiments) before the cap device 130 is advanced toward the medicine cartridge 120 to create the fluid output path. As such, the relatively small amount of medicine dispensed during the initial "break away" movement of the plunger 125 in the medicine cartridge 120 may be dispensed through the output port 135 and into the infusion set tubing 129 (FIG. 2) to at least partially prime the tubing 129. The pump device 100 may be controlled to perform a subsequent priming operation to fully prime the remaining portion of the infusion set tubing 129.

Accordingly, a number of functions can be performed when the cap device 130 is being coupled to the pump housing 110. Some of these functions may include initialization and preparatory functions, including but not limited to: retaining the medicine cartridge 120 in the cavity 116 of the pump housing 110 (described in connection with FIG. 7A), providing a water-tight seal for the cavity 116 of the pump housing 110 (described in connection with FIGS. 7A and 7C), forcing the plunger 125 of the medicine cartridge 120 to secure to a piston rod (described in connection with FIG. 7B), piercing the septum 121 of the medicine cartridge 120 to provide a flow path for the medicine (described in connection with FIG. 7C), and providing a "break away" force to initiate movement of the plunger 125 in the medicine cartridge 120 (described in connection with FIG. 7D).

Figure 8A:
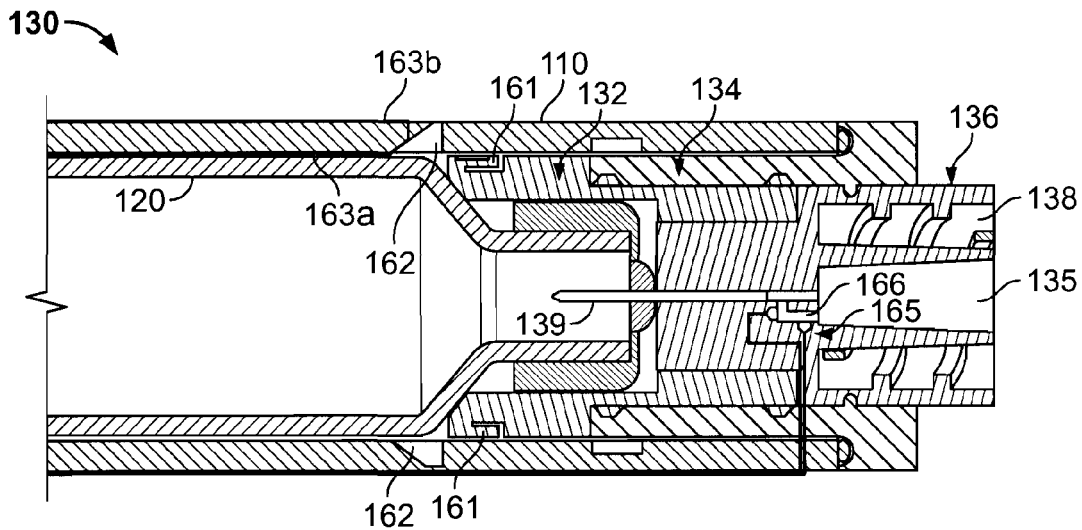
FIGS. 8A-B are cross-sectional views of a portion of the infusion pump system of FIG. 1, in accordance with further embodiments.
Figure 8B:
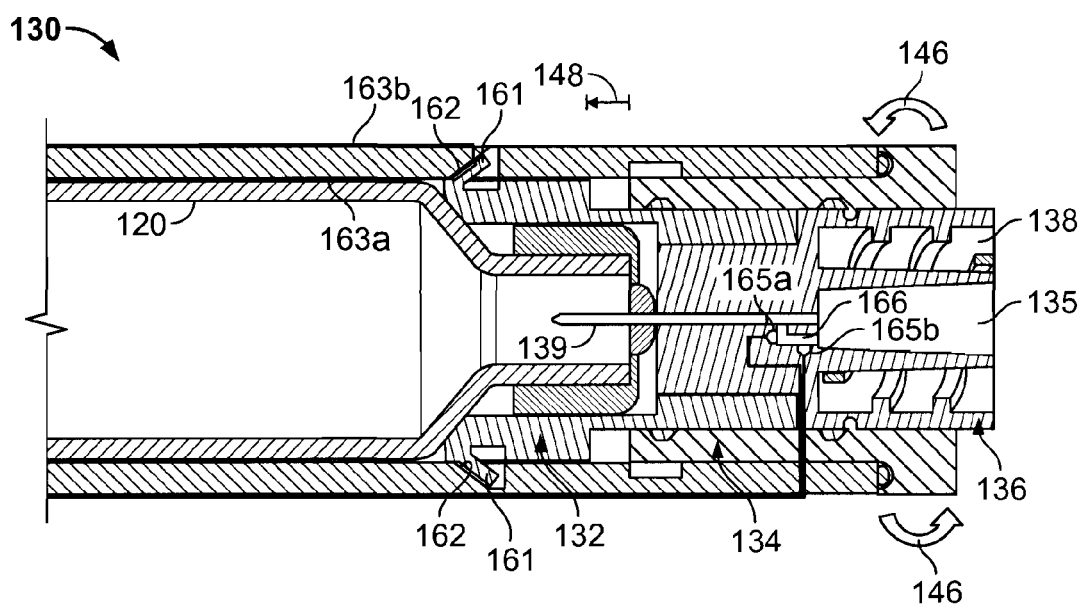

Referring now to FIGS. 8A-B, in some embodiments, the process of coupling the cap device 130 to the pump housing 110 may result in a number of safety related functions also being performed. For example, attachment of the cap device 130 to the pump housing can cause the medicine cartridge 120 to be "locked" in the pump housing 110, thereby encouraging disposal of the pump device 100 after exhaustion of the medicine cartridge. As shown in FIGS. 8A-B, a portion of the cap device 130 may include locking tabs 161 that mate with corresponding notches 162 in the pump housing 110 when the cap device 130 is received by the pump housing 110 at a particular depth. In this embodiment, the locking tabs 161 are formed as part of the slider component 132 of the device 130 so that the tabs 161 are spring biased to extend outwardly. As such, when the slider component 132 is advanced into the cavity 116 (FIG. 3) of the pump housing 110, the locking tabs 161 adjust inwardly toward the longitudinal axis of the slider component 132 (refer, for example, to FIG. 8A). When the locking tabs 161 reach the corresponding notches 162 in the wall of pump housing 110, the locking tabs 161 adjust outwardly into the notches 162 (refer, for example to FIG. 8B). In this embodiment, the locking tabs 161 may be advanced to reach the corresponding notches 162 in when the longitudinal movement of the fluid path component 136 (due to the rotation 146 of the rotator component 134) further causes the longitudinal displacement 148 of the slider component 132, as previously described in connection with FIG. 7D.

Due to the engagement of the locking tabs 161 in the notches 162, the slider component 132 of the cap device 130 is retained in the pump housing 110 in a manner that hinders removal of the medicine cartridge 120. Accordingly, the cap device 130 can be secured to the pump housing 110 in a manner that encourages disposal of the pump device 100 after exhaustion of the medicine cartridge 120. Such a configuration may be useful, for example, in circumstances in which the pump device 100 is designed to be a "one time use" disposable unit. Thus, the cap device 130 may facilitate a "one time use" disposable pump device, thereby reducing the likelihood of failure due to non-intended repeated use of the disposable pump device.

It should be understood from the description herein that, in other embodiments, the locking tabs 161 may be arranged on other components of the cap device 130, such as the rotator component 134 or the fluid path component 136. Also, in other embodiments, the locking mechanism may be in a form other than the locking tabs 161 and corresponding notches 162. For example, the locking mechanism may include an adhesive engagement that prevents removal of the cap device 130 after attachment to the pump housing 110, a unidirectional thread pattern that permits tightening but hinders loosening, or the like.

In another example of a safety related function, if the cap device 130 is improperly engaged with the pump housing 110, the medicine dispensation can be shutdown. As shown in FIGS. 8A-B, the cap device 130 may be used to close a circuit loop that indicates when the cap device is engaged with the pump housing 110 in a particular position. In this embodiment, the circuit loop includes a first conductive line 163a and a second conductive line 163b that extend along the pump housing 110 and are separated by a gap in the previously described notch 162. The gap between the first and second conductive lines 163a-b creates a break in the sensor circuit that can be closed when the locking tabs 161 reach the corresponding notches 162 in the wall of pump housing 110. In this embodiment, one of the locking tabs 161 can be used to close the circuit loop due to a conductive pad 164 disposed on the outer surface of the locking tab. When the locking tab 161 is adjusted to mate with the corresponding notch 162 (as previously described), the electrical circuit through the first line 163a, the conductive pad 164, and the second line 163b can be closed, thereby indicating that the cap device 130 is properly engaged with the pump housing 110 at a particular depth. The electrical circuit that includes the conductive lines 163a-b may be a part of (or communicate with) a sensor circuit arranged within the pump device 100 (FIG. 1) or within the removable controller 200 (FIG. 1).

Accordingly, if the cap device 130 is secured with the pump housing 110 in a proper manner, the controller device 200 may be operated to dispense medicine from the medicine cartridge 120. If, however, the cap device 130 is improperly oriented or becomes dislodged relative to the pump housing 110, the electrical circuit loop (e.g., through the first line 163a, the conductive pad 164, and the second line 163b) may become open to indicate such a misalignment to the controller device 200 (FIG. 1). In response to such an indication, the controller device 200 may prevent medicine dispensation (e.g., cease activation of the drive system) and communicate an alarm to the user. Such a configuration permits the user with an opportunity to correctly attach the cap device 130 to the pump housing 110 and thereafter restart safe dispensation of the medicine.

It should be understood from the description herein that, in other embodiments, the electrical circuit loop (e.g., through the first line 163a, the conductive pad 164, and the second line 163b) may be arranged on other components of the cap device 130, such as the rotator component 134 or the fluid path component 136. Also, in some embodiments, other devices can be used to detect the proper attachment of the cap device 130 to the pump housing 110. For example, the cap device 130 may be used to actuate a position sensor that indicates when the cap device is engaged with the pump housing 110 in a particular position. Alternatively, an optical sensor can be used in combination with a light emitted from the controller device 200 (FIG. 1) to indicate when the cap device 130 is engaged with the pump housing 110 in a particular position.

In yet another example of a safety related function, attachment of the cap device 130 to the pump housing 110 can cause a flow sensor to be arranged along the medicine flow path to detect the flow (or nonflow) of medicine from the pump device 100. As shown in FIGS. 8A-B, the cap device 130 may house at least a portion of a flow sensor 165 that is configured to detect the flow of medicine through the cap device 130 or to detect an occlusion in the fluid path. In this embodiment, the flow sensor 165 may be arranged within or adjacent to a bypass fluid path 166. A portion of the medicine that is dispensed from the medicine cartridge 120 may be redirected through the bypass fluid path 166 for detection by the flow sensor 165. The bypass fluid path 166 has an outlet that is in communication with the output port 135 of the cap device 130. In some embodiments, the bypass fluid path 166 may have a substantially smaller diameter than the primary fluid path between the needle penetrator 139 and the output port 135.

The flow sensor 165 may be used to detect when an occlusion exists in the fluid path between the medicine cartridge 120 and the infusion site on the user's skin. Such an occlusion may occur, for example, when the infusion set tubing 129 (FIG. 2) is kinked. If the medicine dispensation path to the user is occluded, the user may receive no dosage or a lower dosage of the medicine. As such, the flow sensor 165 housed in the cap device 130 can be used to indicate when the fluid is flowing or not flowing, thereby permitting the controller device 200 (FIG. 1) to communicate an alarm to the user if an occlusion exist.

In some embodiments, the flow sensor 165 housed at least partially in the cap device 130 may include electrodes 165a and 165b that are arranged to detect fluid flow through the bypass fluid path 166. For example, an AC current may be passed through the fluid between the electrodes 165a-b, and the electrodes 165a-b can be configured to sense the electrical admittance (e.g., the inverse of the electrical impedance) through the fluid in the bypass fluid path 166. The electrical admittance sensed using the electrodes 165a and 165b can be correlated to a fluid velocity (e.g., a change in the flow speed causes a change in the electrical admittance). In such embodiments, the controller device 200 (FIG. 1) may be programmed to correlate the fluid velocity from the electrical admittance sensed using the electrodes 165a and 165b. If the fluid velocity falls below a threshold value, the controller device 200 may communicate an alarm to the user that an occlusion exists in the fluid path. When the cap device 130 is attached with the pump housing 110 in a particular position, the flow sensor 165 may be in electrical communication with the controller device 200 (FIG. 1) via one or more electrical lines that extend along the pump housing 110 (refer, for example, to FIG. 8B).

In an alternative embodiment, the flow sensor 165 housed at least partially in the cap device 130 may include a pressure sensor that indicates the fluid pressure in the bypass fluid path 166. For example, a miniature pressure transducer can be arranged in the cap device 130 to detect the fluid pressure. In some cases, the miniature pressure transducer can be formed as a MEMS (Micro-ElectroMechanical System) device. The miniature pressure transducer may be output an electrical signal that can be correlated to a fluid pressure value. In such embodiments, the controller device 200 (FIG. 1) may be programmed to correlate the fluid pressure from the signal output by the pressure transducer. If the fluid pressure increases above a threshold value, the controller device 200 may communicate an alarm to the user that an occlusion exists in the fluid path. The fluid passing through the cap device 130 may act directly upon the pressure transducer, or alternatively, the fluid passing through the cap device may act upon a miniature piston device or diaphragm device that in turn acts upon the pressure transducer.

It should be understood from the description herein that, in alternative embodiments, other types of flow sensors can operate within the cap device 130 to detect flow (or nonflow) of the medicine. For example, the flow sensor 165 may include a first probe and a second probe arranged in the cap device 130—the first probe being used to induce a small oxygen ($O_2$) concentration into the fluid flow, and the second probe being used to detect the oxygen level in the fluid flow. If the second probe detects an oxygen concentration greater than a threshold level, the fluid flow may be occluded or partially occluded. As such, the controller device 200 may communicate an alarm to the user that an occlusion exists in the fluid path. In another example, the flow sensor 165 may include an optical sensor device arranged in a flow path (e.g., bypass flow path 166) of the cap device 130. The optical sensor may respond to a laser light that is emitted from the reusable controller device 200 (FIG. 1) proximate the cap device 130. In some circumstances, the optical sensor device may deform when the fluid pressure increases above a threshold level, thereby providing a different response to the laser light (e.g., reflecting or bending the light in a different manner that indicates a fluid pressure greater than the threshold level). Such detection of an increased fluid pressure in the cap device 130 can indicate that an occlusion exists in the fluid path, and the controller device 200 the controller device 200 may communicate an alarm to the user.

Referring now to FIGS. 9-10, the pump device 100 may include a piston rod 370 that is configured to attach with the medicine cartridge 120. For example, as previously described in connection with FIG. 7B, a longitudinal force 140 may be applied to the medicine cartridge 120 during engagement of the cap device 130 to the pump housing 110. This longitudinal force 140 can be used to urge a portion of the medicine cartridge 120 (e.g., the plunger 125 in this embodiment) to secure to a plunger engagement device 375 (FIG. 10) of the piston rod 370. In some embodiments, the plunger engagement device 375 may include penetration members 376 that penetrate into the plunger 125 of the medicine cartridge 120 and thereby secure the medicine cartridge 120 to the piston rod 170. (It should be understood that FIG. 9 depicts the piston rod 370 arranged in the pump housing 110 of the pump device 100, and FIG. 10 shows a similar view with the pump housing 110 and other portions removed for purposes of illustrating the piston rod 370 and medicine cartridge 120.)

As shown in FIG. 9, the pump device 100 may include a drive system 300 that is controlled by the removable controller device 200 (FIGS. 1-2). Accordingly, the drive system 105 can accurately and incrementally dispense fluid from the pump device 100 in a controlled manner. The drive system 300 may include the flexible piston rod 370 that is incrementally advanced toward the medicine cartridge 120 so as to dispense the medicine from the pump device 100. In this embodiment, at least a portion of the drive system 300 is mounted to the pump housing 110, and a detachable shell 112 covers at least a portion of the drive system 105. The detachable shell 112 may include an inner curved surface against which a curved section of a piston rod 370 rests. A cover mount 113 may be assembled to the pump housing 110 to secure some components of the drive system 300 with the pump housing 110, and the "unused" or retracted portion of the piston rod 370 may rest in a channel defined in the top of the cover mount 113. Some embodiments of the drive system 300 may include a battery powered actuator (e.g., reversible motor 320 or the like) that resets a ratchet mechanism 330, a spring device 350 that provides the driving force to the ratchet mechanism 330, and a drive wheel 360 that is rotated by the ratchet mechanism 330 to advance the flexible piston rod 370 toward the medicine cartridge 120. The operation of the drive system 300 is described in more detail below in connection with FIGS. 26-30. Previously filed U.S. patent application Ser. No. 11/522,560 (incorporated herein by reference) describes further drive system configurations for use in an infusion pump device.

Referring to FIG. 10, in some embodiments, the flexible piston rod 370 comprises a plurality of segments 372 serially connected by hinge portions 373 so that the flexible piston rod 370 is adjustable from a curved shape to a noncurved shape. The plurality of segments 372 and the interconnecting hinge portions 373 can be integrally formed in one piece from one or more moldable materials, including polymer materials such as Nylon or POM. In this embodiment, each of the plurality of rod segments 372 includes an exterior thread pattern 374 along at least one cylindrical surface portion. The plunger engagement device 375 can be arranged at a forward end of the piston rod 370. As such, the plunger engagement device 375 faces toward the medicine cartridge 120 when the medicine cartridge 120 is inserted into the cavity 116.

The plunger engagement device 375 is configured to attach to the plunger 125 of the medicine cartridge 120 when urged together. For example, as previously described in connection with FIG. 7B, a longitudinal force 140 may be applied to the medicine cartridge 120 during engagement of the cap device 130 to the pump housing 110. This longitudinal force 140 can be used to urge the medicine cartridge 120 (and the plunger 125 therein) toward the plunger engagement device 375. In this embodiment, the plunger engagement device 375 includes a plurality of penetration members 376 that extend from a pusher disc 378 toward the plunger 125 and are configured to penetrate into the plunger 125 in response to the longitudinal force 140 (FIGS. 7B and 10). Thereafter, the plunger 125 may remain secured to the piston rod 370 during operation of the pump device 100.

Figure 11:
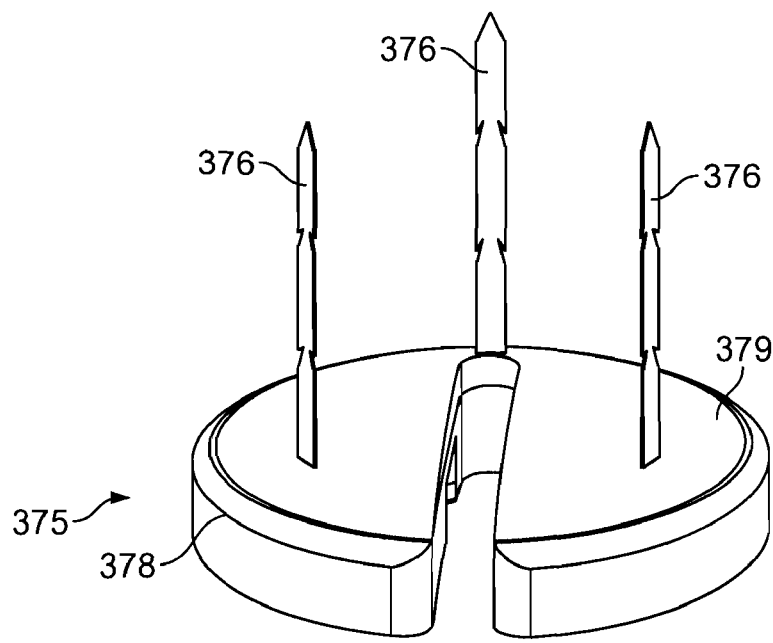
FIG. 11 is a perspective view of a plunger engagement device of the piston rod of FIG. 10.
Figure 12:
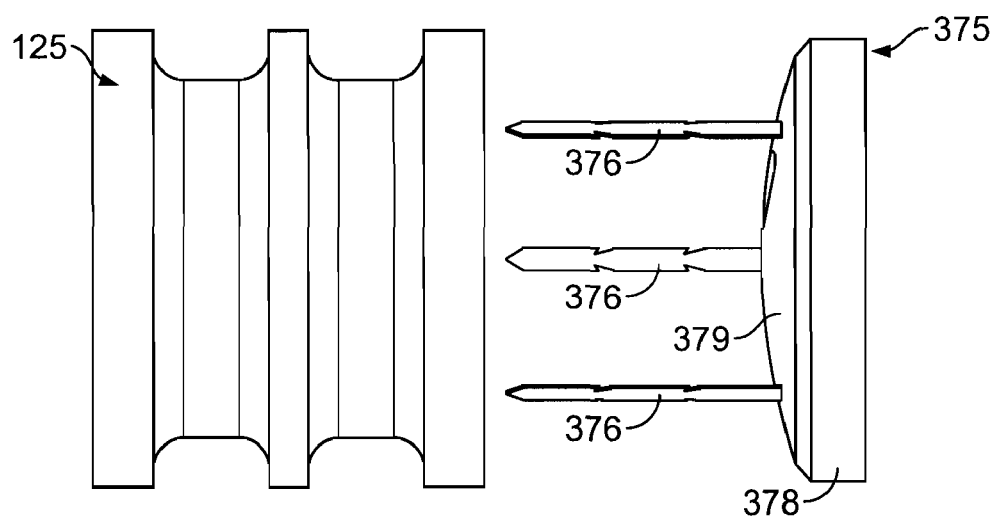
FIG. 12 is a side view of the piston rod and the medicine cartridge plunger of FIG. 10.

Referring to FIGS. 11-12, in some embodiments, the penetration members 376 may comprise rigid blades having pointed tips to pierce into the rear face of the plunger 120 (e.g., the "dry" face of the plunger 125 opposite the "wet" face). The penetration members 376 may extend for a length that is slightly less than the axial length of the plunger 125. In such circumstances, the penetration members 376 do not penetrate through the front face (e.g., the "wet" face) of the plunger 125. The rigid blades may include serrations or another retention portion that enhances the engagement with the plunger 125 and hinders separation of the plunger 125 from the penetration members 376. Also, in this embodiment, the pusher disc 378 includes a protruding spherical surface 379 that is configured to press against the rear face of the plunger 125 (FIG. 12). In some circumstances, the center core of the plunger 125 may be urged forward more than the radial surfaces of the plunger 125 (due to the frictional engagement with the inner wall of the medicine cartridge 120). Accordingly, the protruding surface 379 of the disc 378 may promote full contact with the rear face of the plunger 125 during advancement of the plunger 125 within the cartridge 120.

In some embodiments, the penetration members 376 can reduce the compliance of the plunger material and thereby increase the dosage accuracy. For example, the plunger 125 may comprise an elastomer material that exhibits flexibility and compliance when it is urged longitudinally relative to the inner wall of the medicine cartridge 120 (e.g., the center of the plunger is urged forward while the outer radial surfaces flex due to the frictional engagement with the inner wall of the medicine cartridge). Such compliance may create a level of unpredictability between the piston rod movement and the corresponding plunger movement. The penetration members 376 can pierce into the plunger 125 and thereby serve as generally rigid inserts that reduce the compliance exhibit by the plunger 125. In some circumstances, the penetration members 376 can serve as inserts that provide greater uniformity between the piston rod movement and the corresponding plunger movement. As such, the pump device 100 may have increased accuracy for the dosage of medicine that is dispensed in response to an incremental movement of the piston rod 370.

Furthermore, the penetration members 376 can reduce the likelihood of accidental medicine delivery when the pump device 100 undergoes an impact (e.g., when the pump device is dropped on the ground). The penetration members 376 secure the plunger 125 to the drive system (e.g., to the piston rod 370 in this embodiment), so the plunger 125 does not necessarily become displaced when the medicine cartridge 120 is impacted. For example, if the pump device 100 is dropped on the ground and undergoes an impact, the plunger 125 may be retained in its position relative to the wall of the cartridge due to the attachment with the piston rod 370. As such, the likelihood of the plunger 125 moving slightly relative to the inner wall of the medicine cartridge 120 (and thereby forcing some medicine from the cartridge) in response to an impact may be reduced.

It should be understood from the description herein that, in some embodiments, the penetration members 376 can reduce the compliance of the plunger 125 so that the pusher disc 378 need not include a protruding spherical surface (e.g., surface 379 in FIG. 12). Rather, the pusher disc 376 may include a generally flat surface that pushes against the rear face of the plunger 125 (as shown, for example, in FIGS. 13A-D).

Figures 13A, 13B:
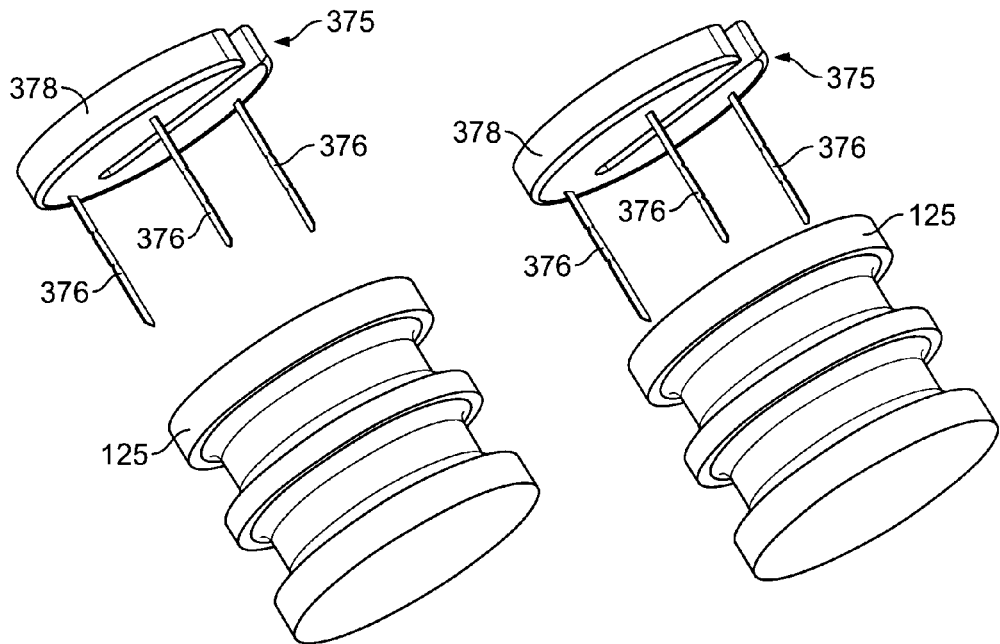
FIGS. 13A-D are perspective views of a plunger engagement device of a piston rod and a medicine cartridge plunger, in accordance with some embodiments.
Figures 13C, 13D:
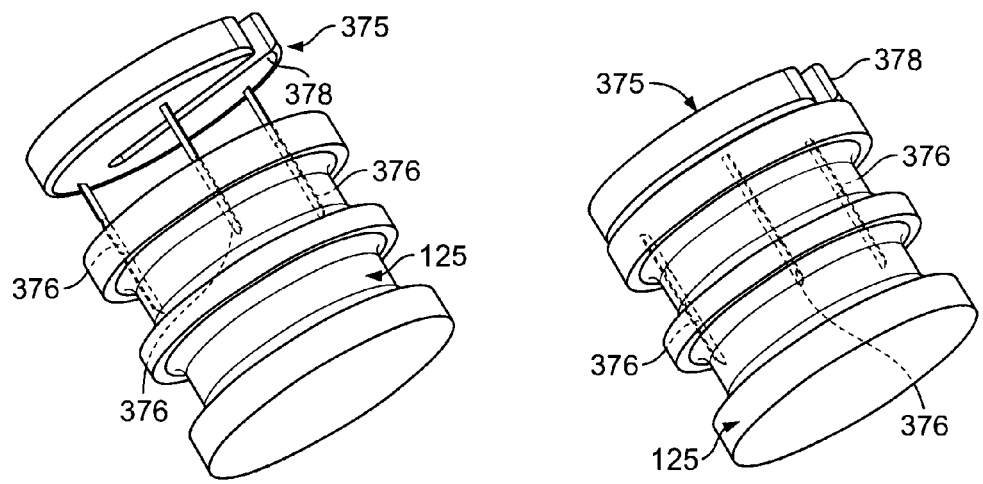

Referring to FIGS. 13A-D, in operation, the plunger engagement device 375 can be secured to the plunger 125 to reduce or prevent relative motion between the plunger 125 and the pusher disc 378 and to reduce the compliance of the plunger 125. As previously described in connection with FIG. 7B and FIG. 10, a longitudinal force 140 may be applied to the medicine cartridge 120 during engagement of the cap device 130 to the pump housing 110. This longitudinal force 140 is used to urge the medicine cartridge 120 (and the plunger 125 therein) toward the penetration members 376 of the plunger engagement device 375. As the plunger 125 continues its motion toward the pusher disc 378 in response to the longitudinal force 140, the penetration members 376 can pierce into the rear face of the plunger 125. The insertion of the penetration members 376 may continue until the rear face of the plunger 125 abuts the pusher disc 378. As shown in FIG. 13D, the penetration members 376 do not penetrate through the front face (e.g., the "wet" face) of the plunger 125 in this embodiment.

In this embodiment, the plunger engagement device 375 includes three penetration members 376 that are laterally offset from the center of the pusher disc 378. The penetration members 376 comprise rigid blades or knife-like pins that include serrations to facilitate engagement with the plunger 125. These rigid blades may be laterally offset from the center of the pusher disc 378 so as to pierce the rear face of the plunger 125 in an outer radial portion of the plunger 125 (e.g., a portion of the plunger that might otherwise be more compliant during advancement of the plunger 125 inside the cartridge 120).

It should be understood from the description herein that, in other embodiments, the plunger engagement device 375 may have a different configuration. For example, as shown in FIGS. 14A-B, some embodiments of the plunger engagement device 375 may include penetration members 382 in the form of pin inserts. These penetration members 382 can include a generally straight shaft and pointed tip to facilitate penetration into the rear face of the plunger 125 (FIG. 14B). In another example, as shown in FIGS. 15A-B, some embodiments of the plunger engagement device 375 may include penetration members 384 in the form of radially curved blades. Such embodiments of the penetration members 384 may include generally flat blade shafts that are curved about a longitudinal axis. The radial curvature of the penetration members 384 may reflect the radial distance from the central longitudinal axis of the plunger 125 (FIG. 15B). In yet another example, as shown in FIGS. 16A-B, some embodiments of the plunger engagement device 375 may include penetration members 386 in the form of generally flat blades without serrations. These penetration members 386 may include a pointed tip to facilitate insertion into the plunger 125 (FIG. 16B). In a further example, the plunger engagement device 375 may include an adhesive layer arranged on the pusher disc 378 so that the pusher disc 378 becomes adhered to the rear face of the plunger 125.

In some embodiments in which the plunger engagement device 375 includes penetration members having serrations or other retention portions, the retention portions may be formed in a number of configurations. For example, as shown in FIG. 17, some embodiments of the plunger engagement device 375 may include penetration members 387 having straight-cut retention portions that hinder separation of the plunger 125 away from the plunger engagement device 375. In another example, as shown in FIG. 18, some embodiments of the plunger engagement device 375 may include penetration members 388 having angled-cut retention portions.

Some embodiments of the plunger engagement device 375 may include one penetration member, two penetration members, three penetration members (as previously described in connection with FIGS. 11-12 and 13A-D), four penetration members, five penetration members, or more. Moreover, the penetration members may be arranged on the plunger engagement device 375 in a number of different configurations so as to penetrate the plunger 125 at different locations. For example, as shown in FIG. 19, some embodiments of the plunger engagement device 375 may include only one penetration member (depicted here in the form of a pin insert penetration member 382 described in FIGS. 14A-B). In this embodiment, the single penetration member 382 is arranged to pierce the rear face of the plunger 125 proximate to the central axis of the plunger 125. In another example, as shown in FIG. 20, some embodiments of the plunger engagement device 375 may include two penetration members (again, depicted here in the form of a pin insert penetration member 382 described in FIGS. 14A-B). In this embodiment, the pair of penetration members 382 are offset from the central axis of the plunger 125 and oriented approximately 180° from one another. As such, the penetration members 382 can pierce into the rear face of the plunger 125 on generally opposite sides of the central axis of the plunger 125. In a further example, as shown in FIG. 21, some embodiments of the plunger engagement device 375 may include four penetration members 382 that are offset from the central axis of the plunger 125 and oriented approximately 90° from one another. In yet another example, as shown in FIG. 21, some embodiments of the plunger engagement device 375 may include five penetration members 382 that are offset from the central axis of the plunger 125 and oriented approximately 72° from one another.

Some embodiments of the plunger engagement device 375 may include penetration members that are not oriented circumferentially equidistant to one another. For example, as shown in FIG. 23, some embodiments of the plunger engagement device 375 may include four penetration members 382 that are spaced apart in two pairs. A first pair of the penetration members 382 are spaced apart from the second pair of penetration members 382. As such, the first and second pairs of the penetration members 382 can pierce into the rear face of the plunger 125 on generally opposite sides of the central axis of the plunger 125.

Also, some embodiments of the plunger engagement device 375 may include combinations of the previously described configurations. For example, as shown in FIG. 24, some embodiments of the plunger engagement device 375 may include a first penetration member 382 arranged to pierce the rear face of the plunger 125 proximate to the central axis of the plunger 125 (similar to that shown in FIG. 19) and four addition penetration members 382 that are offset from the central axis of the plunger 125 and oriented approximately 90° from one another (similar to those shown in FIG. 21).

Some embodiments of the piston rod 370 may include a plunger engagement device 380 that penetrates along the outer circumferential surface of the plunger 125. For example, as shown in FIG. 25, the plunger engagement device 380 may include a cylindrical penetration member 381 that is integral with the pusher disc portion. The cylindrical penetration member 381 can penetrate along the outer circumferential surface of the plunger 125 (e.g., through the outer rings of the plunger 125 or between the outer rings and the cartridge wall) when the plunger 125 is urged toward the piston rod 370. In this example, the cylindrical penetration member 381 bypasses the first two outer rings of the plunger 125 so that at least a portion of the load on the third ring is directly transmitted to the plunger engagement device 380. As such, the plunger engagement device 380 can be used to retain the plunger 125 relative to the piston rod 370 and to reduce the compliance of the plunger 125 when being advanced inside the medicine cartridge 120.

Referring now to FIGS. 26-30, the drive system 300 of the pump device can be controlled to accurately dispense fluid from the pump device 100. As previously described in connection with FIGS. 9-10, the drive system 300 may include the flexible piston rod 370 that is incrementally advanced toward the medicine cartridge 120 so as to dispense the medicine from the pump device 100. The drive system 300 may also include an electrically powered actuator (e.g., reversible motor 320 or the like) that is coupled to a guided pusher arm 325 (FIGS. 28-30), which is used to adjust a ratchet mechanism 330 to a reset position. A spring device 350 (FIGS. 28-30) stores potential energy when the ratchet mechanism 330 is adjusted to the reset position and thereafter drives the ratchet mechanism 330 to a forward position to advance the piston rod 370 and dispense the medicine. The motor 320 can be decoupled from the ratchet mechanism 330 during the drive step. Accordingly, the reversible motor 320 is used to shift the ratchet mechanism to a reset position, but the motor 320 does not drive the ratchet mechanism 330 to the forward position.

In those embodiments in which the pump device 100 is connected to a removable controller device 200 (FIGS. 1-2), the controller device 200 can communicate control signals to the drive system 300 or other components of the pump device

Figure 26:
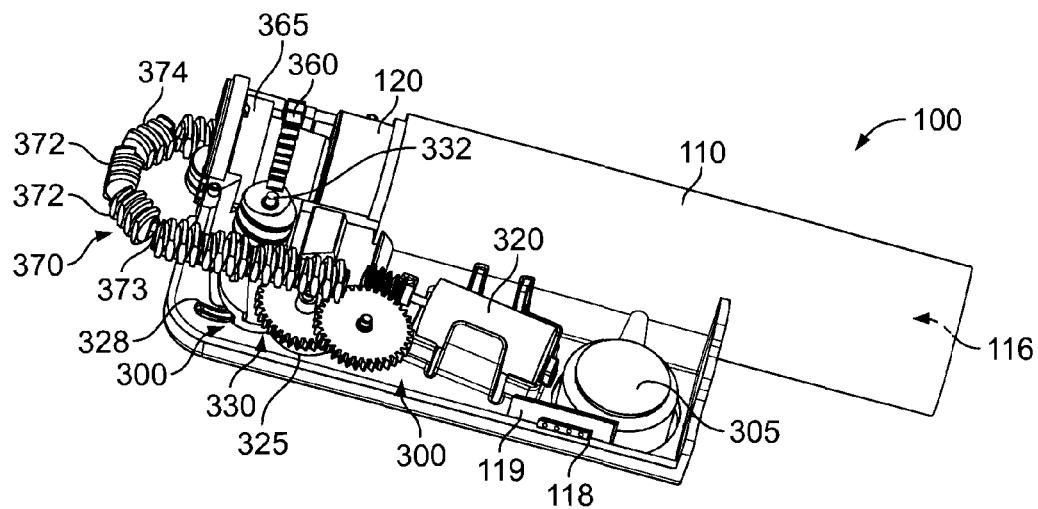
FIG. 26 is perspective view of an pump device, with some portions removed to view a drive system.

100. As previously described, the controller device 200 can include a controller housing structure 210 (FIGS. 1-2) that is configured to mate with a complementary portion of the pump housing structure 110 so as to form a mechanical connection. In such circumstances, the pump device 100 may include on or more electrical contacts 118 (FIG. 26) that are exposed to the controller device 200 and that mate with opposing electrical contacts (e.g., pads, pins, or the like) on the adjacent face of the controller device 200. In this embodiment, the electrical contacts 118 are disposed on a connection circuit 119 (FIG. 26). The connection circuit 119 may be simple and inexpensive so as to facilitate a low-cost pump device 100 that is disposable. The connection circuit 119 can be in electrical communication with one or more components housed in the pump device 100, such as the motor 320, the battery 305, one or more sensor devices, or a combination thereof). The connection circuit 119 facilitates electrical communication with the removable controller device 200 (FIGS. 1-2). As such, the controller device 200 is capable of transmitting electrical signals to the pump device 100 and is capable of receiving feedback signals (e.g., sensor signals) from the components in the pump device 100.

As shown in FIG. 26, some components of the drive system 300 can be retained by the pump housing 110. For example, the motor 320, the pusher arm 325, the ratchet mechanism 330, and the spring device 350 can be assembled into the pump housing 110 and then retained by the cover mount 113 (FIG. 9). Also, the drive wheel 360 and an adjacent bearing 365 (to facilitate rotation of the drive wheel 360 relative to the pump housing 110) can be received in annular channels of the pump housing 110. In this embodiment, a locking pawl 342 (FIGS. 28-30) is integrally formed with the pump housing 110 so as to align with a portion of the ratchet mechanism 330 when the ratchet mechanism 330 is assembled onto the pump housing 110. When the cover mount 113 (FIG. 9) is assembled to the pump housing 110, the cover mount 113 can align and retain the ratchet mechanism 330 and other components of the drive system 300. In such a construction, the assembled pump housing 110 can permit the desired motion of the components of the drive system 300 while reducing the likelihood of "backlash" movement or component dislodgement (which might otherwise occur, for example, when the pump device 100 is dropped to the ground).

Figure 27:
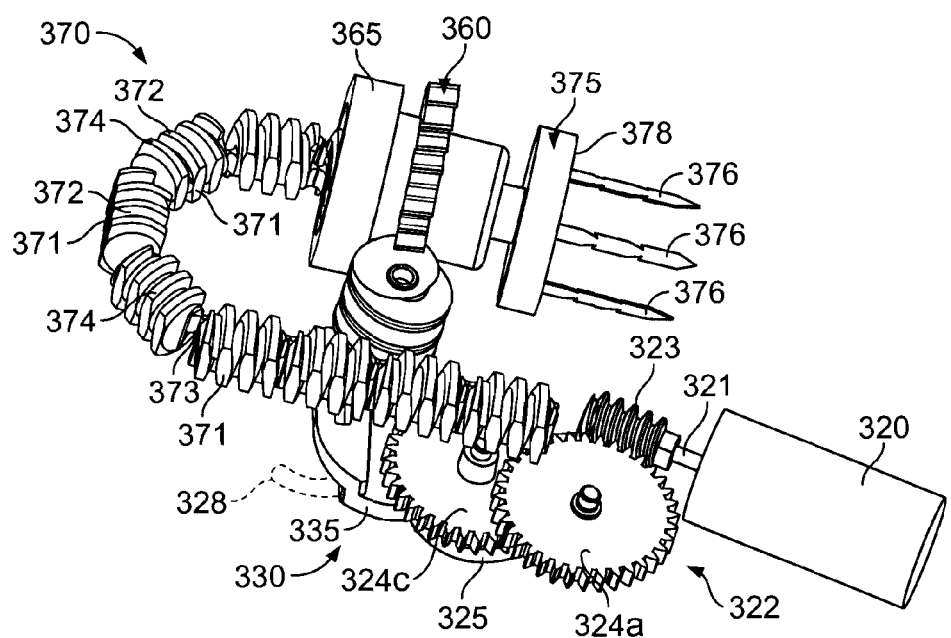
FIG. 27 is a perspective view of the drive system of the pump device of FIG. 26, in accordance with some embodiments.

Referring to FIGS. 27-30, in some embodiments of the drive system 300, the reversible motor 320 is used to shift the ratchet mechanism 330 to the reset position, yet the motor 320 can be decoupled from the ratchet mechanism 330 during the drive step that causes dispensation of medicine. Briefly, the motor 320 can be used to act upon the pusher arm 325, which is guided along a predetermined path in a guide slot 328. In this embodiment, the guide slot 328 is integrally formed in an inner wall of the pump housing 110 (refer to FIG. 26), and the pusher arm 325 includes a slider pin 326 that mates with the guide slot 328. (It should be understood that FIG. 26 depicts the drive system 300 mounted to the pump housing 110 of the pump device 100, and FIG. 27 shows a similar view with the pump housing 110 removed for purposes of illustrating components of the drive system 300.) After the pusher arm 325 is advanced in the guide slot 328 so that the ratchet mechanism 330 is adjusted to the reset position (refer to FIG. 29 in which the ratchet mechanism 330 is reset to engage a new tooth on the ratchet body 340), the motor 320 can reverse direction and promptly retract the pusher arm 325 to the first position (refer to FIG. 30 in which the pusher arm 325 is retracted). The spring device 350 provides the energy for the drive step that advances the piston rod 370 and dispenses medicine, but the drive step may occur over a period of time that is greater than the relatively quick retraction of the pusher arm 325 to the first position. In such circumstances, the pusher arm 325 may be temporarily separated from the ratchet mechanism 330, thereby causing the motor to be decoupled from the ratchet mechanism 330 during the drive step. Accordingly, the drive system 300 can provide an efficient process for accurately and reliably dispensing medicine in a manner that conserves battery life. Moreover, the drive system 300 may comprise few, if any, high-cost actuator components or electronics, thereby facilitating the production of a disposable and reliable pump device 100.

Referring now in more detail to the components of the drive system 300 depicted in FIGS. 27-30, the electrically power actuator may be in the form of the motor 320 having a rotatable output shaft 321. In this embodiment, the motor 320 is reversible in that can receive signals that cause the output shaft 321 to rotate in a first rotational direction or in a second, opposite rotational direction. One example of a suitable motor 320 is a coreless DC motor with reversible rotation capabilities, as supplied by Mabuchi Motor Co. of Japan. As previously described, the operation of the motor 320 can be controlled by a control device (e.g., removable control device 200 as described in connection with FIGS. 1-2 or the like) via electrical signals communicated through one or more electrical contacts.

Still referring to FIGS. 27-30, a gear system 322 may be coupled to the motor 320 so that actuation by the motor 320 causes the pusher arm 325 to act upon the ratchet mechanism 330 or to decouple from the ratchet mechanism 330. In this embodiment, the gear system 322 includes a worm gear 323 and a gear reduction assembly comprising spur gears 324*a*, 324*b*, and 324*c*. The pusher arm 325 can be pivotably coupled to the gear 324*c* so that partial rotation of the gear 324*c* causes the pusher arm to reciprocate within the guide slot 328. Accordingly, rotation of the motor 320 in a first direction can be translated into an advancement force to the pusher arm 325. The advancement force on the pusher arm 325 is applied to a pawl member 335, which (in this embodiment) causes the pawl member 335 to pivot to a reset position (refer to FIG. 29). In addition, rotation of the motor 320 in a second direction can be translated into an retraction force to the pusher arm 325, which can cause the pusher arm 325 to be separated from the pawl member 335 during the drive step (refer to FIG. 30).

Figure 29:
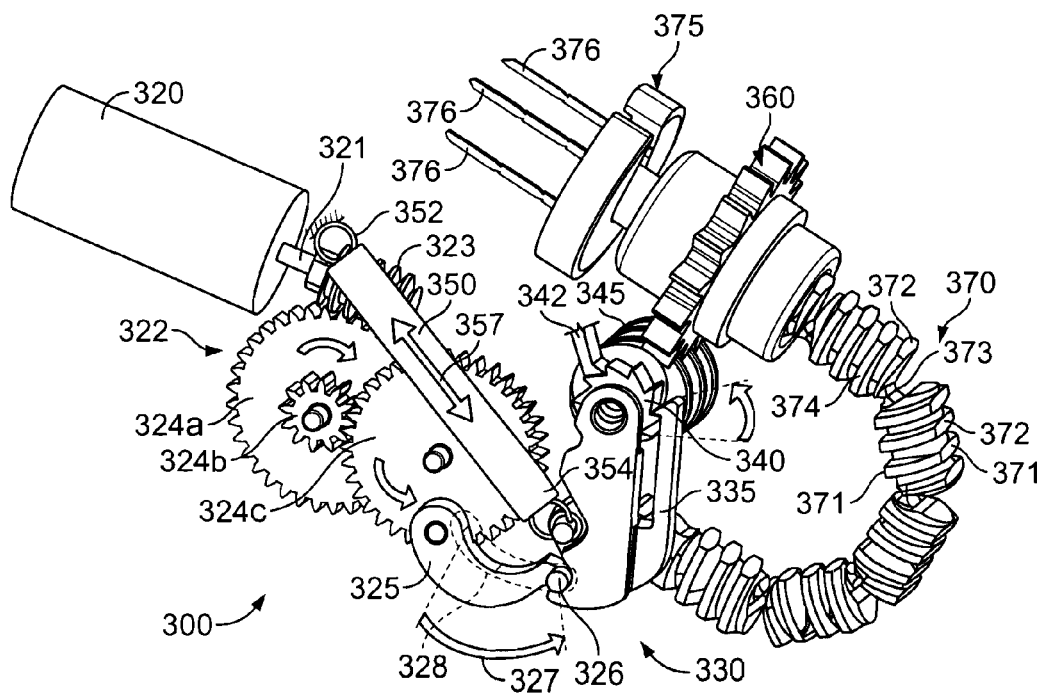
FIG. 29 is a perspective view of the drive system of FIG. 27 in a second position.

As such, the motor 320, the gear system 322, and the pusher arm 325 can collectively operate as an actuator assembly that provides a reliable and consistent adjustment of the ratchet mechanism 330 during a reset step (refer to FIG. 29). Moreover, this actuator assembly (e.g., the motor 320, the gear system 322, and the pusher arm 325) can be activated to separate from the pawl member 335, thereby permitting the motor 320 to decouple from the ratchet mechanism 330 during a drive step (refer to FIG. 30).

The motion path of the pusher arm 325 can be configured to provide an efficient mechanical advantage orientation during the desired motion of the adjustable pawl member 335. In this embodiment, the pusher arm 325 is directed by a guide slot 328 formed in the pump housing 10 (FIG. 26). In particular, the pusher arm 325 includes the slider pin 326 that is received within the guide slot 328 during assembly. The portion of the pusher arm 325 proximate the slider pin 326 can abut against the pawl member 335 when the pusher arm is advanced. As such, when a first end of the pusher arm 325 is moved by the gear 324*c*, a second end of the pusher arm (proximate the slider pin 326) is directed by the guide slot 328. The orientation of the pusher arm 325 relative to the guide slot 328 can be configured to provide an efficient mechanical advantage for the pushing force applied by the pusher arm 325 during the desired motion of the adjustable pawl member 335.

Still referring to FIGS. 27-30, the ratchet mechanism 330 includes the pawl member 335 and a ratchet body 340, which in this embodiment is a ratchet wheel having a number of teeth along its circumferential surface. In this embodiment, the ratchet wheel 340 is coupled with a worm gear 345, and incremental rotation of the ratchet wheel 340 causes rotation of a drive wheel 360 (due to engagement with the worm gear 345). The pawl member 335 is adjustable between a reset position (refer to FIG. 29) and a forward position (refer to FIG. 28). For example, during the reset step, the motor 320 may be activated to advance the pusher arm 325 (guided by the guide slot 328), and the pusher arm 325 then applies a pushing force that adjusts the pawl member 335 to the reset position in which the pawl member 335 grabs a new tooth of the ratchet wheel 340 (refer to FIG. 29). In this embodiment, the adjustable pawl member 335 is pivotably coupled to about the axis of an axle 332 (refer to FIG. 26) that receives the ratchet wheel 340 and the worm gear 345.

Figure 28:
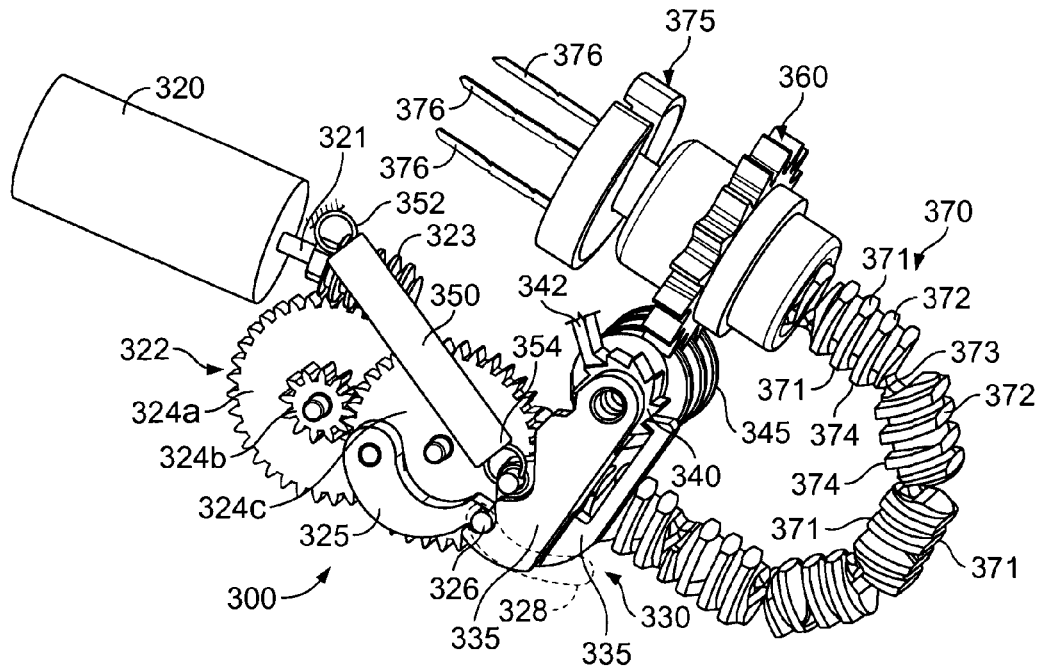
FIG. 28 is another perspective view of the drive system of FIG. 27 in a first position.

A spring device 350 is also coupled to the pawl member 335 so as to urge the pawl member 335 toward the forward position (refer to FIG. 28). In this embodiment, the spring device 350 is in the form of a coil spring that is fixed to the pump housing 110 (not shown in FIGS. 27-30) at a first end portion 352 and that is engaged with the pawl member 335 at a second end portion 354. Thus, as shown in FIG. 29, when the pawl member 335 is adjusted to the reset position, the spring device 350 is in tension and stores potential energy that urges the pawl member 335 to return to the forward position (refer to FIG. 28) and thereby drive the ratchet wheel 340 in a forward rotational direction. As previously described, a locking pawl 342 (FIGS. 28-30) can be used to prevent the ratchet wheel 340 from reverse motion. The locking pawl 342 can flex or otherwise adjust to permit the incremental forward rotation of the ratchet wheel 340. As such, the adjustable pawl member 335 can adjust from the forward position (refer to FIG. 28) to the reset position (refer to FIG. 29) to engage a new tooth of the ratchet wheel 340 while the ratchet wheel 340 remains in position due to the locking pawl 342.

It should be understood that the drive system 300 can employ a set of location sensors to indicate when the pawl member 335 has reach the reset position or the forward position. For example, these sensors can be optical, magnetic, or contact-type sensors. The sensors may be capable of transmitting signals that indicate when the location of one of the gears in the gear system 322, the pusher arm 325, or the pawl member 335 is detected. Such sensor signals may be transmitted to the motor 330, to the controller device 200 (FIGS. 1-2), or a combination thereof. In one embodiment, the pawl member 335 may be equipped with an electrically conductive contact that engages a first contact-type sensor when moved to the reset position and that engages a second contact-type sensor when moved to the forward position. As such, the first and second contact-type sensors can electrically communicate with the motor 330, the controller device 200, or both when the pawl member reaches the reset and forward positions. These signals may be used to indicate when the motor 330 should cease rotation or reverse rotation.

Still referring to FIGS. 27-30, in some embodiments the ratchet wheel 340 can be integrally formed with the worm gear 345 so that the incremental rotation of the ratchet wheel 340 is translated to the worm gear 345. Such rotation of the worm gear 345 causes rotation of the drive wheel 360. The drive wheel 360 includes a central aperture having an internal thread pattern therein (not shown in FIGS. 27-30), which mates is an external thread pattern 374 on the rod segments 372. Thus, the incremental motion provided by the ratchet mechanism 330, the pusher arm 325, and the motor 320 causes the drive wheel 360 to incrementally rotate, which in turn translates to a longitudinal advancement of the flexible piston rod 370.

Accordingly, in some embodiments, the piston rod 370 may undergo only forward or positive longitudinal displacement as a result of drive system 300. For example, the drive system 300 substantially hinders the piston rod 370 from retracting or "backing up" in response to fluid pressure in the medicine cartridge 120 or other reversal forces. In such circumstances, the flexible piston rod 370 can be retracted only upon disassembly of the pump device 300 (e.g., to disengage the drive gear 360 or the ratchet mechanism 330). In those embodiments in which the pump device 100 is intended to be disposable, the non-retractable piston rod configuration may facilitate a "one time use" disposable pump device, thereby reducing the likelihood of failure due to non-intended repeated use of the disposable pump device 100.

Still referring to FIGS. 27-30, the flexible piston rod 370 can comprise a plurality of rod segments 372 serially connected by hinge portions 373 so that the flexible piston rod 370 is adjustable from a curved shape to a noncurved shape. As previously described, the plurality of segments 372 and the interconnecting hinge portions can be integrally formed in one piece from one or more moldable materials, including a number of polymer materials. In this embodiment, the plurality of segments 372 comprise generally cylindrical segments that have an exterior thread pattern 374 along at least one cylindrical surface portion. As previously described, the plunger engagement device 375 can be arranged at a forward end of the piston rod 370 so that the plunger engagement device 375 faces toward the medicine cartridge 120.

In some embodiments, the flexible piston rod 370 can include an anti-rotation structure that hinders the piston rod 370 from rotating with the drive wheel 360 (thereby allowing the rotation of the drive wheel 360 to translate into a longitudinal motion of the piston rod 370). For example, in this embodiment, the flexible piston 370 includes longitudinal flat surfaces 371 extending along each of the segments 372. The longitudinal flat surfaces 371 can engage a complementary surface on the pump housing 110 (not shown in FIGS. 27-30) proximate the drive wheel 360 so that the flexible piston rod 370 is hindered from rotating when the drive wheel 360 turns. Accordingly, the longitudinal flat surfaces 371 on each segment 372 aligns to form a keyway that receives a mating key (e.g., a complementary flat surface) on the pump housing. In other embodiments, the anti-rotation structure may include one or more longitudinal channels 173 (with each channel capable of engaging an associated protrusion that acts as a key to hinder rotation while permitting longitudinal motion) or the like. Previously filed U.S. patent application Ser. No. 11/522,836 (incorporated herein by reference) describes further piston rod configurations for use in an infusion pump device.

Because the flexible piston rod 370 is adjustable from a curved shape to a noncurved shape, the overall length of the pump device can be reduced in some embodiments. For example, in a typical infusion pump that houses a straight and rigid rod, the typical infusion pump requires a package or housing having a linear dimension sufficient to accommodate the length of the rigid piston rod when it is at its limit of travel in which it is fully withdrawn from the container or cylinder. The pump device 100 incorporating the flexible piston rod 370 can require less space than a similar device that houses a non-flexible, rigid rod.

Figure 30:
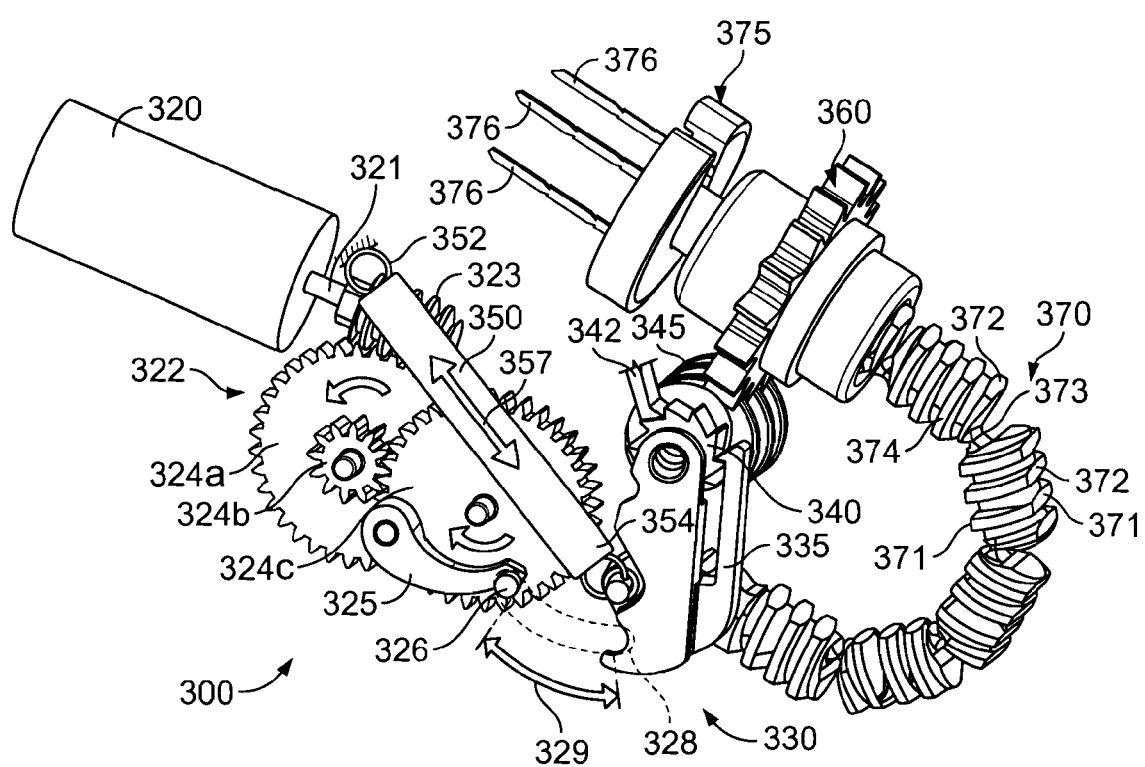
FIG. 30 is a perspective view of the drive system of FIG. 27 while returning to the first position.

Referring now to FIGS. 28-30, the incremental motion cycle of the drive system 300 may include rotation of the motor 320 so that the pusher arm 325 is advanced from a first position to act upon the pawl member 335 and then retracted back to the first position. Such movement of the pusher arm 325 can cause the pawl member 335 to adjust from the forward position (refer to FIG. 28), to the reset position (refer to FIG. 29), and back to the forward position (under the driving force of the spring device 350). The adjustment of the pawl member 352 from the reset position to the forward position drives the ratchet wheel 340 and worm gear 345, which incrementally rotates the drive wheel 360 and thereby advances the flexible piston rod 370 a longitudinal increment distance. In one example, the drive system 300 can advance the piston rod 370 a longitudinal increment distance of about 16 microns or less (about 4 microns to about 12 microns, about 5 microns to about 9 microns, and preferably about 6 microns to about 8 microns) for each incremental motion cycle of the ratchet mechanism 330.

Referring to FIG. 28, in this embodiment of the incremental motion cycle, the pawl member 335 begins at the forward position with the pusher arm 325 retracted in a first position (e.g., the rest position in this embodiment). The adjustable pawl member 335 can be in this forward position, for example, because the drive system 300 previously completed a drive step at an earlier time.

Referring to FIG. 29, in response to the controller device transmitting a signal to initiate the cycle, the motor 320 may begin to rotate in a first rotational direction that advances the pusher arm 325 to push against the pawl member 335. Such movement of the pusher arm 325 causes a pushing force 327 that overcomes the bias of the spring device 350 and adjusts the pawl member 335 toward the reset position (e.g., the reset step). When the adjustable pawl member 335 reaches the reset position, as shown in FIG. 29, the pawl member 335 is capable of engaging a new tooth of the ratchet wheel 340. The locking pawl 342 prevents the ratchet wheel 340 from rotating in a reverse (non-forward) rotational direction while the adjustable pawl member 335 is shifting back to the reset position. Such an adjustment of the pawl member 335 back to the reset position creates a tension force 357 in the spring device 350 (as shown in FIG. 29), thereby storing potential energy to drive the adjustable pawl member 335 and ratchet wheel 340 in a forward rotational direction for the drive step.

Referring to FIG. 30, after the pawl member 335 reaches the reset position, the motor 330 stops rotating in the first rotational direction and reverses to rotate in the second, opposite rotational direction. Such rotation in the second direction by the motor 320 causes the pusher arm 325 to promptly retract to the first position (while guided by the guide slot 328). As such, the spring device 350 begins to urge the pawl member 335 toward the forward position. When the adjustable pawl 335 is driving the ratchet wheel 340 in the forward rotational direction, the potential energy of the spring device 350 is being translated to kinetic energy for the motion of the pawl member 335 and the ratchet wheel 340. Such an adjustment of the pawl member 335 from the reset position to the forward position drives the ratchet wheel 340 and the integrally formed worm gear 345. The incremental rotation of the worm gear 345 results in an incremental rotation by the drive wheel 360, which advances the flexible piston rod 370 a longitudinal increment distance. Such an incremental advancement of the flexible piston rod 370 can cause a predetermined volume of fluid to be dispensed from the cartridge 120. In the event of a subsequent cycle (including the reset step and the drive step), the motor 320 would begin by rotating in the first rotational direction so as to advance the pusher arm 325 yet again. This pattern of cycles may continue until the piston rod 370 has reached the limit of its longitudinal travel.

Still referring to FIG. 30, although the pusher arm 325 can be promptly retracted to the first position due to the reverse rotation of the motor 320, the pawl member 335 is driven to the forward position (FIG. 28) over a greater period of time. This period of time required for the drive step is affected by a number of factors, including the spring force from the spring device 350, the fluid pressure inside the medicine cartridge 120, and the like. Accordingly, the pusher arm 325 can be temporarily separated from the pawl member 335 when it is retracted to its first position, thereby causing the motor 320 to be decoupled from the ratchet mechanism 330 during the drive step. For example, the portion of the pusher arm 325 proximate the slider pin 326 can become temporarily spaced apart by a distance 329 from the pawl member 335 while the pawl member 335 is being driven from the reset position (FIG. 29) to the forward position (FIG. 28). Such a configuration permits the motor 320 to expend a short burst of electrical energy to reset the ratchet mechanism 330 (e.g., during advancement of the pusher arm 325) while contributing no energy during the drive step to drive the ratchet mechanism 330 to the forward position for dispensation of medicine. Because the motor 320 can be decoupled from the ratchet mechanism 330 during the drive step, only the spring device 350 expends energy over a period of time to drive the ratchet mechanism 330 to the forward position. Accordingly, the pump device 100 can reliably and accurately dispense dosages of medicine in a safe and energy efficient manner. In particular, the motor 320 is not required to draw energy from the battery over an extended period of time (e.g., during the drive step in which the piston rod 370 is advanced to dispense medicine over a period of time). Instead, the motor 320 may draw upon the battery power during advancement of the pusher arm 325 to quickly reset the ratchet mechanism 330 and during the brief retraction of the pusher arm 325.

A number of embodiments of the invention have been described. Nevertheless, it will be understood that various modifications may be made without departing from the spirit and scope of the invention. Accordingly, other embodiments are within the scope of the following claims.

What is claimed is:

1. An infusion pump device, comprising:
   a pump housing that defines a space to receive a medicine;
   a drive system to dispense a medicine from the pump housing when the medicine is received in the space, the drive system comprising:
   a ratchet mechanism that advances a piston rod during a drive step to dispense the medicine when the medicine is received in the space; and
   an electrically powered actuator that decouples from the ratchet mechanism during the drive step while the piston rod is advanced and that couples with the ratchet mechanism to provide a reset force to the ratchet mechanism.

2. The infusion pump device of claim 1, wherein the drive system further comprises a spring device that provides a drive force to the ratchet mechanism during the drive step to advance the ratchet mechanism in a forward direction.

3. An infusion pump device, comprising:
   a pump housing that defines a space to receive a medicine;
   a drive system to dispense a medicine from the pump housing when the medicine is received in the space, the drive system comprising:

a ratchet mechanism that advances a piston rod during a drive step to dispense the medicine when the medicine is received in the space; and an electrically powered actuator that decouples from the ratchet mechanism during the drive step, wherein the drive system further comprises a spring device that provides a drive force to the ratchet mechanism during the drive step to advance the ratchet mechanism in a forward direction, and wherein the electrically powered actuator is coupled to the ratchet mechanism during a reset cycle to provide a reset force to the ratchet mechanism.

4. The infusion pump device of claim 3, wherein the electrically powered actuator expends a short burst of electrical energy to reset the ratchet mechanism and contributes no force upon the ratchet mechanism when the spring device advances the ratchet mechanism in the forward direction.

5. The infusion pump device of claim 1, wherein the electrically powered actuator comprises a bi-directional actuator.

6. The infusion pump device of claim 5, wherein the electrically powered actuator comprises a reversible rotational motor.

7. The infusion pump device of claim 1, wherein the drive system further comprises a pusher arm coupled to the electrically powered actuator, wherein the electrically powered actuator decouples from the ratchet mechanism by the pusher arm shifting from abutment with the ratchet mechanism to separation from the ratchet mechanism.

8. The infusion pump device of claim 7, wherein the pusher arm is advanced and retracted by the electrically powered actuator, and at least a portion of the pusher arm movement is directed by a guide slot.

9. The infusion pump device of claim 7, wherein the pusher arm is coupled to the electrically powered actuator via one or more gears.

10. The infusion pump device of claim 1, wherein the space in the pump housing is defined to receive a medicine cartridge that contains the medicine.

11. The infusion pump device of claim 10, wherein the piston rod includes a plunger engagement device that attaches to a plunger of the medicine cartridge when the medicine cartridge is received by the pump housing.

12. The infusion pump device of claim 11, further comprising a cap device that engages the pump housing to retain the medicine cartridge therein when the medicine cartridge is received by the pump housing, wherein when the cap device engages the pump housing, the cap device acts upon the medicine cartridge to urge the plunger into attachment with the plunger engagement device of the piston rod.

13. The infusion device of claim 12, wherein the plunger engagement device comprises one or more penetration members that pierce into a first side of the plunger during attachment of the plunger and the plunger engagement device.

14. An infusion pump device, comprising:
a pump housing that defines a space to receive a medicine;
a drive system to dispense a medicine from the pump housing when the medicine is received in the space, the drive system comprising:
  a drive wheel that rotates to advance a piston rod toward the medicine to dispense the medicine when the medicine is received in the space;
  a ratchet wheel that is incrementally rotated in a forward direction to rotate the drive wheel and thereby advance the piston rod;
  a movable pawl that engages the ratchet wheel, the movable pawl being adjustable from a reset position to a forward position so as to incrementally rotate the ratchet wheel in the forward direction a spring device that urges the movable pawl to adjust from the reset position to the forward position; and
  an actuator assembly that acts upon the movable pawl to force the movable pawl to the reset position and that reverses to separate from the movable pawl when the spring device adjusts the movable pawl from the reset position to the forward position.

15. The infusion pump device of claim 14, wherein the actuator assembly comprises an electrically powered motor and a pusher arm, the pusher arm being adjustable from abutment with the movable pawl to separation from the movable pawl.

16. The infusion pump device of claim 15, wherein the pusher arm is advanced and retracted by the electrically powered actuator, and at least a portion of the pusher arm movement is directed by a guide slot.

17. The infusion pump device of claim 15, wherein actuator assembly further comprises one or more gears that couple the pusher arm the electrically powered actuator.

18. The infusion pump device of claim 15, wherein the electrically powered actuator comprises a bi-directional actuator.

19. The infusion pump device of claim 18, wherein the electrically powered actuator comprises a reversible rotational motor.

20. The infusion pump device of claim 14, wherein the actuator assembly comprises an electrically powered that expends a short burst of electrical energy to force the movable pawl to the reset position and that contributes no force upon the movable pawl when the spring device adjusts the movable pawl from the reset position to the forward position.

21. The infusion pump device of claim 14, wherein the space in the pump housing is defined to receive a medicine cartridge that contains the medicine.

22. The infusion pump device of claim 21, wherein the piston rod includes a plunger engagement device that attaches to a plunger of the medicine cartridge when the medicine cartridge is received by the pump housing.

23. The infusion pump device of claim 22, further comprising a cap device that engages the pump housing to retain the medicine cartridge therein when the medicine cartridge is received by the pump housing, wherein when the cap device engages the pump housing, the cap device acts upon the medicine cartridge to urge the plunger into attachment with the plunger engagement device of the piston rod.

24. The infusion device of claim 23, wherein the plunger engagement device comprises one or more penetration members that pierce into a first side of the plunger during attachment of the plunger and the plunger engagement device.

25. A method of dispensing medicine from the infusion pump device of claim 1, comprising:
resetting the ratchet mechanism in the drive system of the infusion pump device by activating the electrically powered actuator to provide the reset force to the ratchet mechanism;
driving the ratchet mechanism in a forward direction to advance the piston rod during the drive step so as to dispense the medicine from the infusion pump device, wherein the electrically powered actuator is decoupled from the ratchet mechanism during the drive step.

26. The method of claim 25, wherein the ratchet mechanism is driven in the forward direction by a spring device that provides a drive force to the ratchet mechanism.

27. The method of claim 26, wherein the electrically powered actuator expends a short burst of electrical energy to reset the ratchet mechanism and contributes no force to act upon the ratchet mechanism when the spring device advances the ratchet mechanism in the forward direction.

28. The method of claim 25, wherein the electrically powered actuator provides the reset force via a pusher arm that is coupled to the electrically powered actuator, the method further comprising shifting the pusher arm from abutment with the ratchet mechanism to separation from the ratchet mechanism so as to decouple the electrically powered actuator from the ratchet mechanism.

29. The method of claim 28, wherein the pusher arm is coupled to the electrically powered actuator via one or more gears.

30. The method of claim 25, wherein the electrically powered actuator comprises a reversible rotational motor.

31. The infusion pump device of claim 3, wherein the electrically powered actuator comprises a reversible rotational motor.

32. The infusion pump device of claim 3, wherein the drive system further comprises a pusher arm coupled to the electrically powered actuator, wherein the electrically powered actuator decouples from the ratchet mechanism by the pusher arm shifting from abutment with the ratchet mechanism to separation from the ratchet mechanism.

33. The infusion pump device of claim 28, wherein the pusher arm is coupled to the electrically powered actuator via one or more gears.

34. The infusion pump device of claim 3, wherein the space in the pump housing is defined to receive a medicine cartridge that contains the medicine.

* * * * *